US012805870B1

(12) United States Patent
Moubarak et al.

(10) Patent No.: US 12,805,870 B1
(45) Date of Patent: Nov. 24, 2026

(54) KNIFE FIRING SUBSYSTEM AND DIFFERENTIAL ASSEMBLY FOR A SURGICAL STAPLER

(71) Applicant: Cilag GmbH International, Zug (CH)

(72) Inventors: Paul Moubarak, Cincinnati, OH (US); Douglas Marriott, Maineville, OH (US); William Claiborne Ryle, Cincinnati, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 0 days.

(21) Appl. No.: 19/328,841

(22) Filed: Sep. 15, 2025

(51) Int. Cl.
*A61B 17/072* (2006.01)

(52) U.S. Cl.
CPC .................. *A61B 17/07207* (2013.01); *A61B 2017/07285* (2013.01)

(58) Field of Classification Search
CPC ................ A61B 17/07207; A61B 2017/07285
See application file for complete search history.

(56) References Cited

U.S. PATENT DOCUMENTS

| | | | | |
|---|---|---|---|---|
| 11,284,898 | B2 * | 3/2022 | Baxter, III | A61B 17/07207 |
| 2020/0405403 | A1 * | 12/2020 | Shelton, IV | A61B 17/3421 |
| 2020/0405408 | A1 * | 12/2020 | Shelton, IV | A61B 34/30 |
| 2021/0186500 | A1 * | 6/2021 | Shelton, IV | A61B 17/07207 |
| 2022/0249182 | A1 * | 8/2022 | Definis | A61B 17/29 |
| 2023/0414294 | A1 * | 12/2023 | Shelton, IV | A61B 1/000094 |

* cited by examiner

*Primary Examiner* — Himchan Song
(74) *Attorney, Agent, or Firm* — Troutman Pepper Locke LLP

(57) ABSTRACT

The disclosed technology includes a differential assembly for a knife firing subsystem of a surgical instrument. The differential assembly comprising a carrier extending along a longitudinal axis, a pinion gear supported by the carrier and configured to engage with a rack gear in mechanical communication with a push rod, and a fin extending transversely outward from the carrier and configured to support the push rod.

20 Claims, 18 Drawing Sheets

KNIFE FIRING SUBSYSTEM AND DIFFERENTIAL ASSEMBLY FOR A SURGICAL STAPLER

FIELD OF THE INVENTION

The present disclosure relates to surgical instruments and, in various arrangements, to surgical stapling and cutting instruments and staple cartridges for use therewith that are designed to staple and cut tissue.

BACKGROUND

Stapling is a crucial aspect of many surgical procedures, such as gastrointestinal, thoracic, and gynecological surgeries. Robotic surgical systems have gained significant recognition in recent years due to their potential to enhance surgical precision and dexterity. However, the development of a dedicated surgical stapling instrument that integrates seamlessly into the surgical workflow of a multi-purpose robot remains an unmet need for many surgeons.

One limitation in many existing surgical stapling and cutting systems is that the force that the instrument can apply when cutting tissue is limited due to the small size of the components, making the instrument unusable or impracticable for some surgeries. In some cases, this limitation is generally a result of the cutting subsystem being unable to withstand the large forces necessary for driving a knife distally to cut tissue without buckling. This and other issues are addressed by the disclosed technology.

SUMMARY

The disclosed technology includes systems, devices, and subsystems for surgical instruments for robotic surgeries. The surgical instruments include several subsystems that can be independently actuated to provide a specific action, such as closing and opening of an end effector of the stapler, articulation of the end effector, rolling of the end effector, and firing of staples within the end effector.

The disclosed technology includes a differential assembly for a knife firing subsystem of a surgical instrument. The differential assembly comprises a carrier extending along a longitudinal axis, a pinion gear supported by the carrier and configured to engage with a rack gear in mechanical communication with a push rod, and a fin extending transversely outward from the carrier and configured to support the push rod.

The disclosed technology further includes a knife firing subsystem for a surgical instrument comprising: a knife configured to move proximally or distally in an end effector; a push rod in mechanical communication with the knife; a rack gear in mechanical communication with the push rod; a carrier extending along a longitudinal axis; a pinion gear supported by the carrier and configured to engage with the rack gear such that, when the carrier is moved proximally or distally, the knife is moved proximally or distally; and a fin extending transversely outward from the carrier and configured to support the push rod.

DETAILED DESCRIPTION

Figure 1:
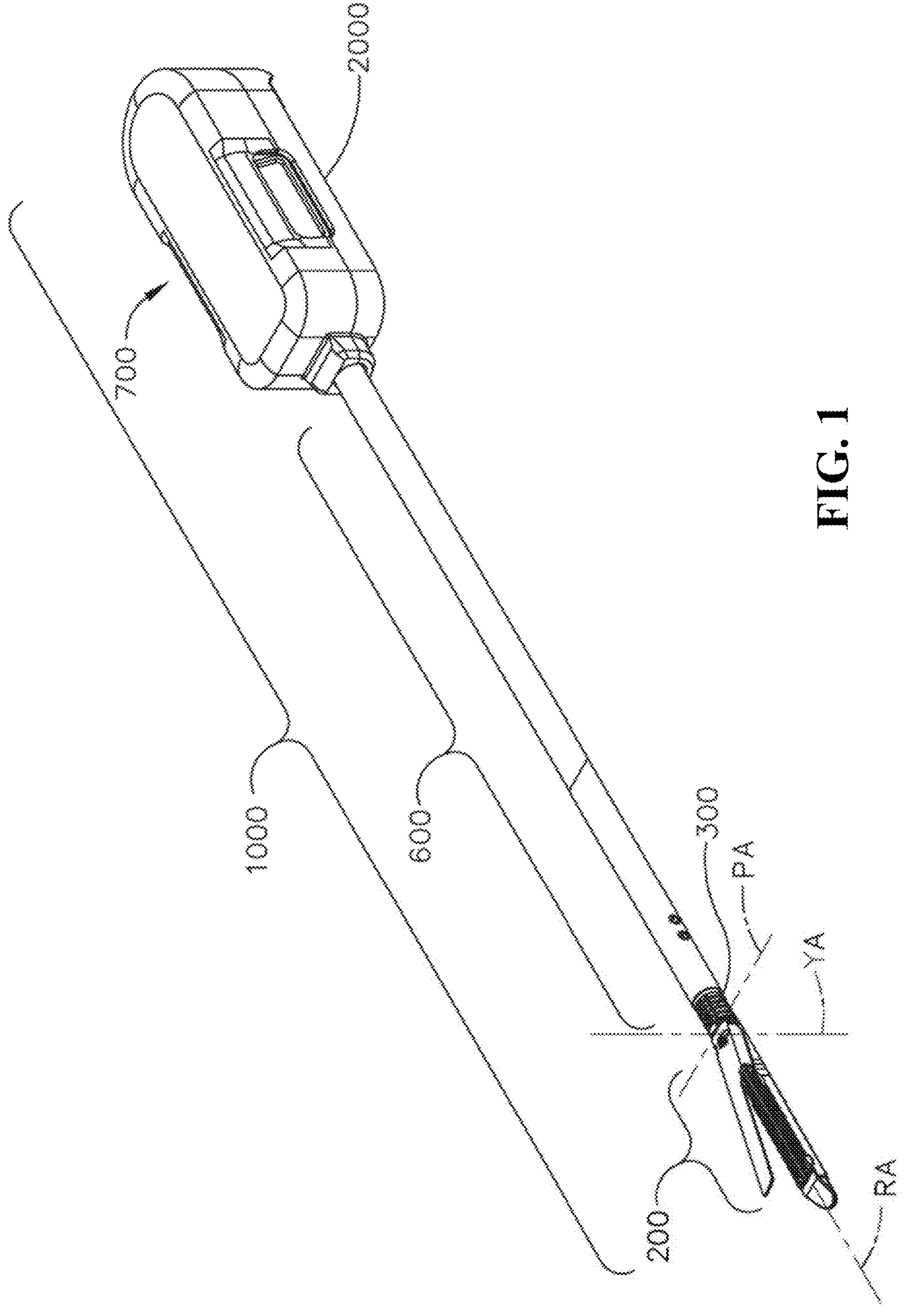
FIG. 1 is a schematic perspective view of a surgical system that includes a surgical instrument, in accordance with the disclosed technology.

As will become apparent throughout this disclosure, the disclosed technology includes a surgical instrument that includes features configured to increase the buckling strength of pushrods used in a firing subsystem of the surgical instrument. In this way, the knife at the end effector is able to cut tissue with a greater force because the pushrods are able to handle a greater force without buckling. The disclosed technology includes fins disposed on a differential that extend transversely with respect to the longitudinal axis and that are configured to restrict transverse movement of the pushrods and prevent buckling. These and other benefits are further described herein.

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±20% of the recited value, e.g., "about 90%" may refer to the range of values from 71% to 99%.

The terms "proximal" and "distal" are used herein with reference to a robotic platform manipulating the housing portion of the surgical instrument. The term "proximal" refers to the portion closest to the robotic platform and the term "distal" refers to the portion located away from the robotic platform. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Furthermore, the use of "couple", "coupled", or similar phrases should not be construed as being limited to a certain number of components or a particular order of components unless the context clearly dictates otherwise.

Also, where alternative examples of certain aspects of the surgical instrument are described, in instances where the same reference numbers as that of previously described examples are used to label components in the alternative example(s), the structure and functionality of those components is the same unless otherwise noted.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, other embodiments are envisioned in which a staple cartridge is not removable from, or at least readily replaceable from, the first jaw. The second jaw comprises an anvil configured to deform staples ejected from the staple cartridge. The anvil is pivotable relative to the first jaw about a closure axis; however, other embodiments are envisioned in which the first jaw is pivotable relative to the second jaw. The surgical stapling system further comprises an articulation joint configured to permit the end effector to be rotated, or articulated, relative to the shaft. Other embodiments are envisioned which do not include an articulation joint. In other words, other elements described herein can be employed in embodiments where no articulation joint is provided without departing from the spirit and scope of the present disclosure. Similarly, the articulation joint can be employed in embodiments where other elements described herein are omitted.

Figure 2:
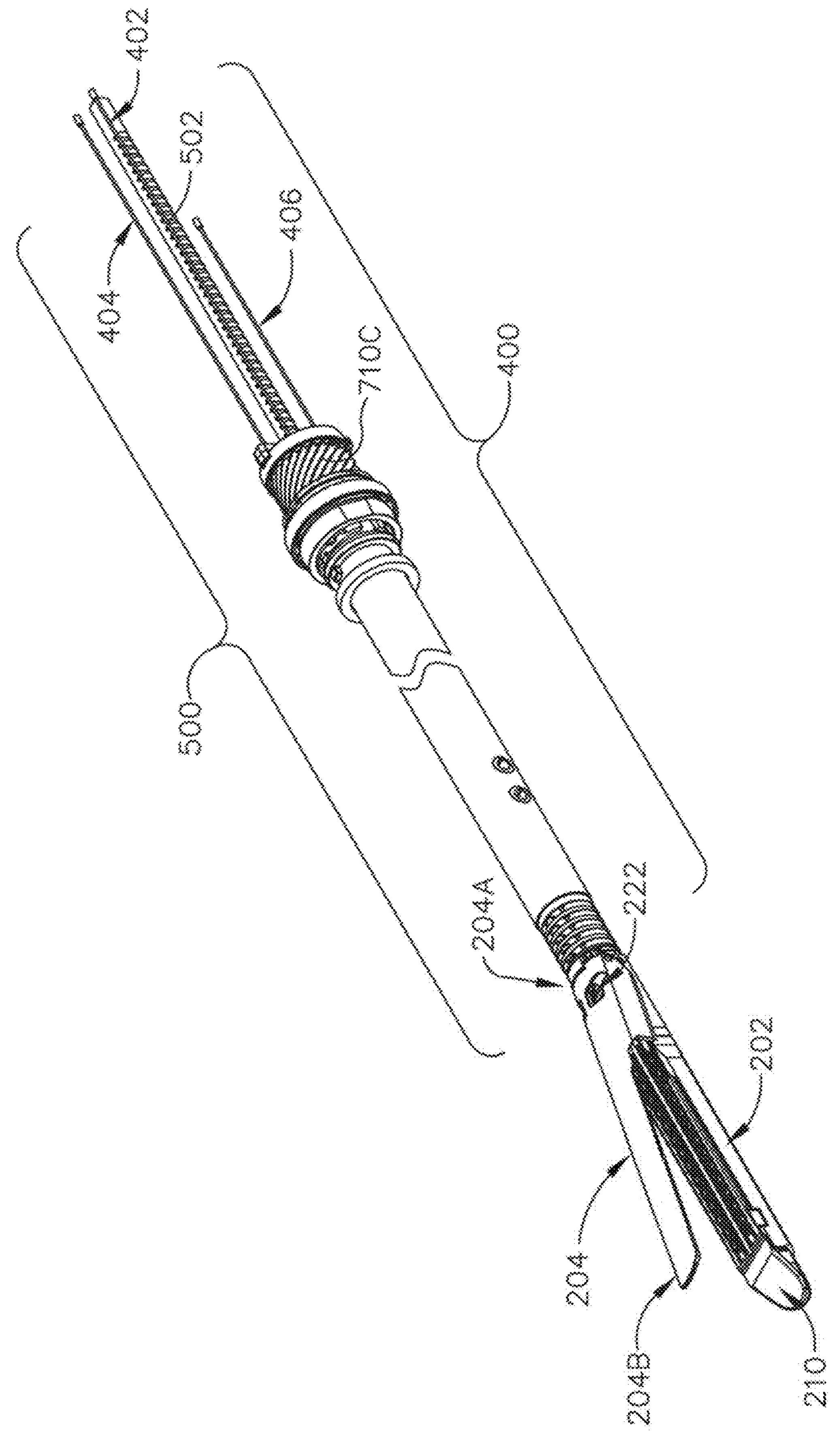
FIG. 2 is a schematic detail view of an end effector, articulation joint, and portions of a cable articulation subsystem, knife firing subsystem, and roll subsystem, in accordance with the disclosed technology.

A surgical instrument 1000 is illustrated in FIG. 1. As discussed in greater detail below, the surgical instrument 1000 is configured to grasp, clamp, incise, and seal patient tissue. The surgical instrument 1000 comprises an end effector 200, an articulation joint 300, an articulation drive subsystem 400 (FIG. 2) configured to articulate the end effector 200 about the articulation joint 300, a knife firing subsystem 500 (FIG. 2) configured to move the end effector between various positions (e.g., an open position, a grasping position, and a clamping position) and to incise and staple patient tissue, a roll subsystem 600 configured to roll the end effector 200 about a roll axis, and a housing 700.

Figures 3A, 3B:
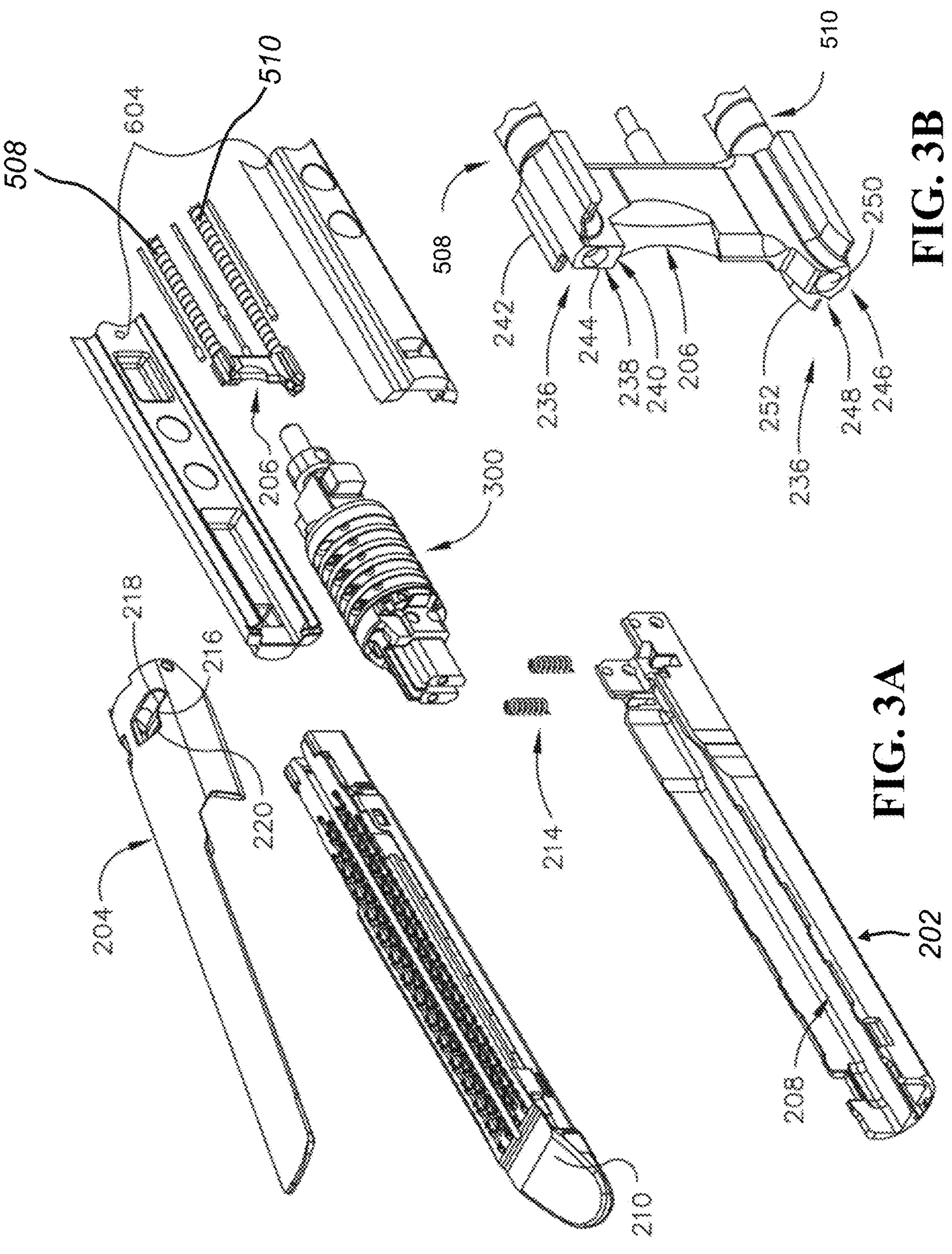
FIG. 3A is a schematic exploded view of a distal end of the surgical instrument, in accordance with the disclosed technology.
FIG. 3B is a schematic detail view of a knife, in accordance with the disclosed technology.

As shown in FIGS. 1-3A, the end effector 200 comprises a first jaw 202 and a second jaw 204 movable between an open position and a closed position. For clarity, first jaw 202 is herein also interchangeably used with "jaw 202" (which is also referred to in the art as a "channel") and second jaw 204 is used interchangeably with "anvil 204". The jaw 202 and anvil 204 may be elongated in form. The jaw 202 defines an elongated channel 208 for receiving a staple cartridge 210. The anvil 204 has a proximal end 204A, a distal end 204B, and a ramp surface 216 defined at the proximal end 204A. The jaw 202 and anvil 204 are pivotally coupled via a pivot pin (not shown) that extends through the jaw 202 and the anvil 204. As seen in FIG. 3A, one or more biasing springs 214 extend between the jaw 202 and anvil 204 to bias the anvil 204 to the open position. The ramp surface 216 may be visible via a kidney bean-shaped opening 222 (which may be formed as part of the manufacturing process to make the ramp surface 216) that has a first lateral end and a second lateral end. In other words, the kidney bean-shaped opening may be open at its lateral ends. The ramp surface 216 forms a lower surface of the kidney bean-shaped opening 222. The ramp surface 216 can be arcuately shaped. For example, it may be upwardly sloped at a first angle 218 and arcuately tapers, in a distal direction, to a substantially horizontal second angle 220. Ramp surface, by way of example, may include a single radius curve, a series of multi-radius curves, a series of multi-radius curves with a series of inflection points, and/or be linearly sloped.

The anvil 204 further defines a longitudinally extending upper knife channel 224 (FIGS. 5A-5D). As shown particularly in FIG. 4, the upper knife channel 224 includes a centrally disposed cylindrical upper knife channel portion 226 and at least one lateral upper knife channel wing 228 that extends away from the upper knife channel portion 226. While the term 'cylindrical' is used, the channel portion 226 need not resemble a perfect cylinder.

Figure 7:
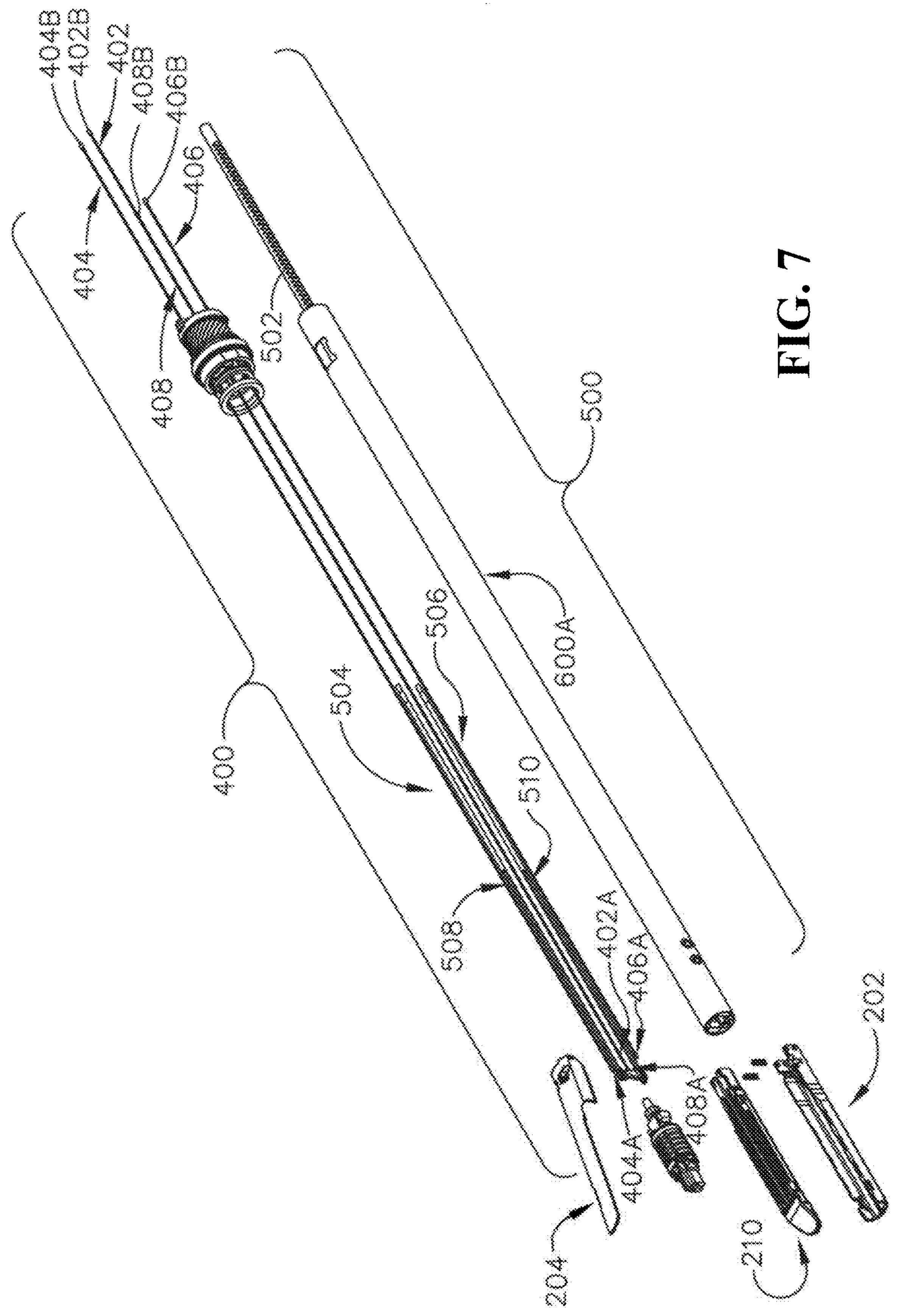
FIG. 7 is a schematic exploded view of the surgical instrument, depicting portions of the cable articulation subsystem, knife firing subsystem, and roll subsystem, in accordance with the disclosed technology.

The surgical instrument 1000 further comprises a knife firing subsystem 500 operable to close the anvil 204 during a closure stroke. After the end effector 200 is closed, the knife firing subsystem 500 (see FIGS. 2 and 7) is operable to incise and staple, with staples from the staple cartridge 210, the patient tissue captured between the staple cartridge 210 (which is retained by the jaw 202) and anvil 204 during a firing stroke.

The knife firing subsystem 500, explained further below in greater detail, includes a knife 206 as shown in FIG. 3B. The knife 206 is coupled to or integral with a knife sled 236. The knife sled 236 is the non-cutting element of the knife 206, and is also referred to as an I-beam. The knife sled 236 includes an upper knife tab 238 and a lower knife tab 246. The upper knife tab 238 includes a centrally disposed cylindrical upper knife tab portion 240 and at least one upper knife tab lateral wing 242 that extends away from the upper knife tab portion 240. While the term 'cylindrical' is used, the tab portion need not resemble a perfect cylinder. In some embodiments, the upper knife tab 238 includes a pair of lateral wings 242 configured to slidably ride in the upper knife channel 224 to move the anvil 204 between the open position, the grasping position, and the clamping position. Each lateral wing 242 may include a ramped surface 242A that engages the anvil ramp surface 216. The upper knife tab portion 240 defines an upper knife tab opening 244 that is configured to receive a barrel crimp coupled to a center cable 512, which is described in greater detail below. The lower knife tab 246 includes a centrally disposed cylindrical lower knife tab portion 248 and at least one lower knife tab lateral wing 250 that extends away from the lower knife tab portion 248. While the term 'cylindrical' is used, the lower knife tab portion 248 need not resemble a perfect cylinder. In some embodiments, the lower knife tab 246 includes a pair of lateral wings 250. The lower knife tab portion 248 defines a lower knife tab opening 252 that is configured to receive a barrel crimp coupled to a center cable 514.

The staple cartridge 210 comprises a cartridge body. In use, the staple cartridge is positioned on a first side of the tissue to be stapled, within the channel 208 of the jaw 202, and the anvil 204 is positioned on a second side of the tissue. The anvil 204 is moved toward the staple cartridge 210 to compress and clamp the tissue against the deck of the staple cartridge 210. Thereafter, staples removably stored in the cartridge body can be deployed into the tissue. The cartridge body includes staple cavities defined therein wherein staples are removably stored in the staple cavities. In some embodiments, the staple cavities are arranged in six longitudinal rows. In some embodiments, three rows of staple cavities are positioned on a first side of a lower knife channel 230 and three rows of staple cavities are positioned on a second side of lower knife channel 230.

Figure 4:
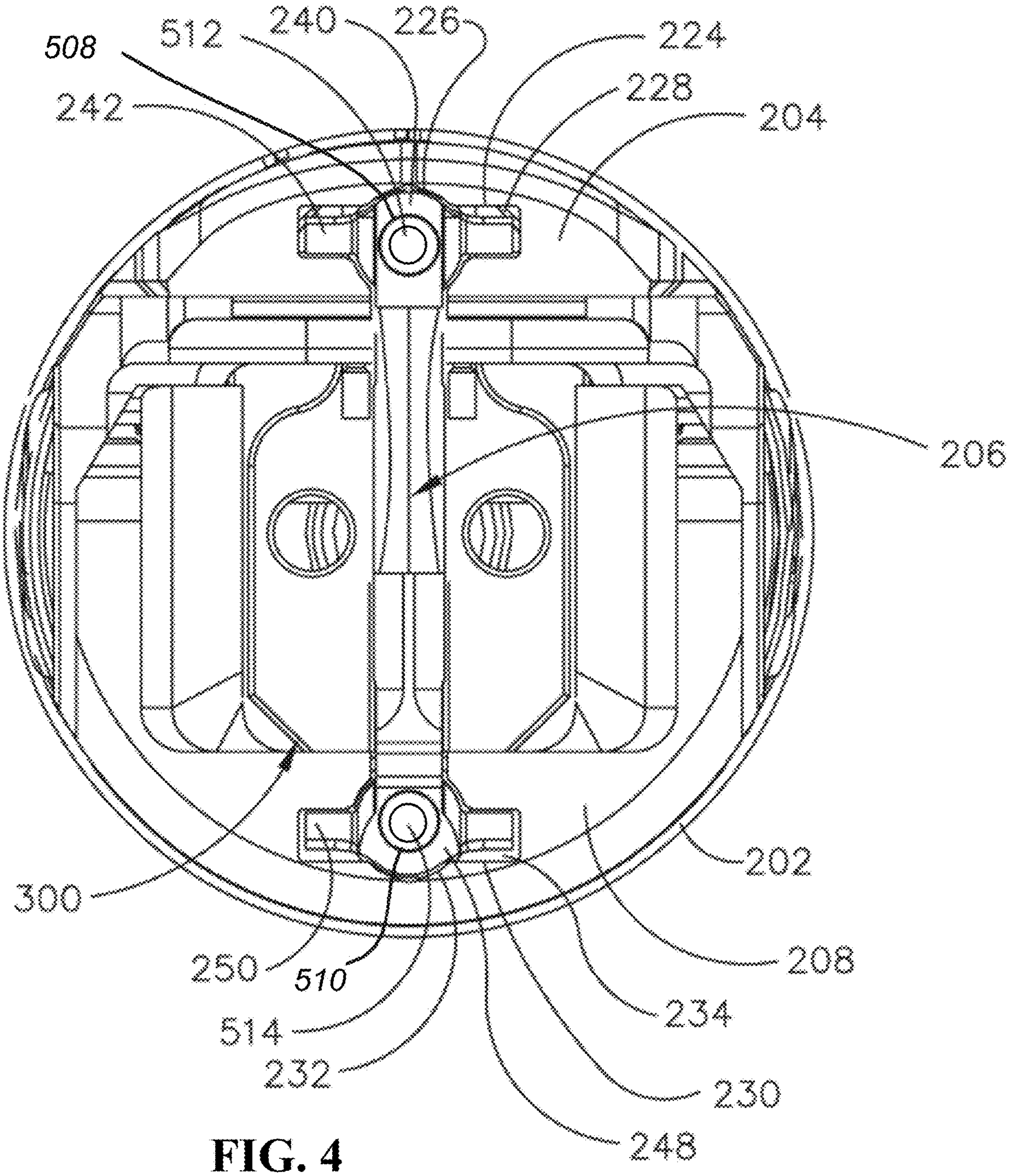
FIG. 4 is a schematic detail front view of the end effector, in accordance with the disclosed technology.
Figure 5A:
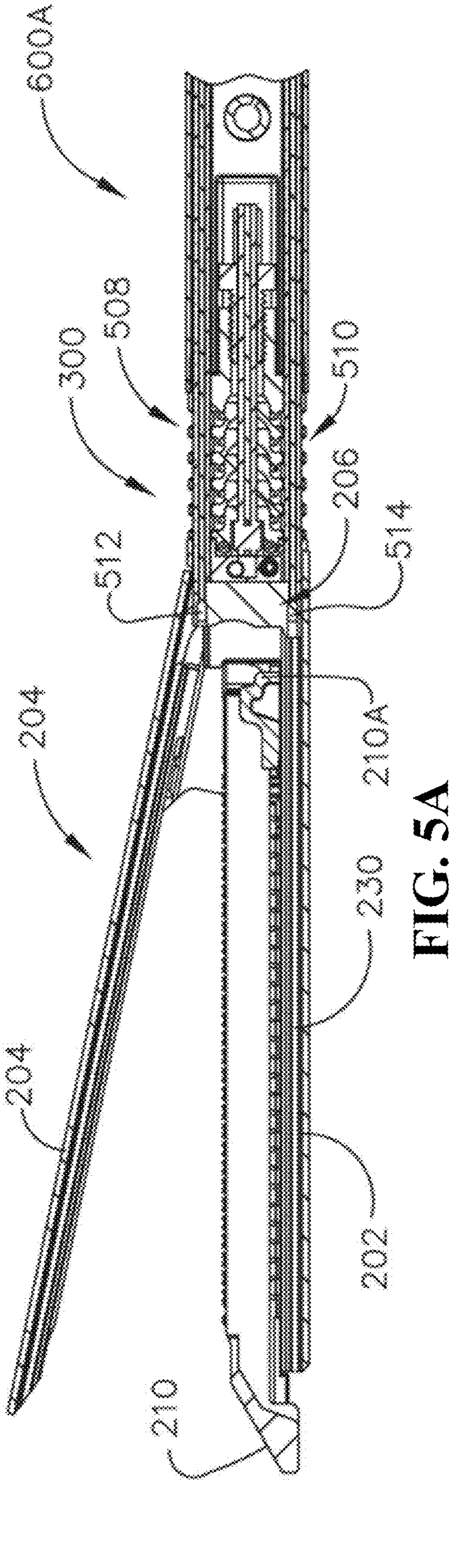
FIG. 5A is a schematic side cross-sectional view of the distal end of the surgical instrument, depicting the anvil in an open position, in accordance with the disclosed technology.
Figure 5B:
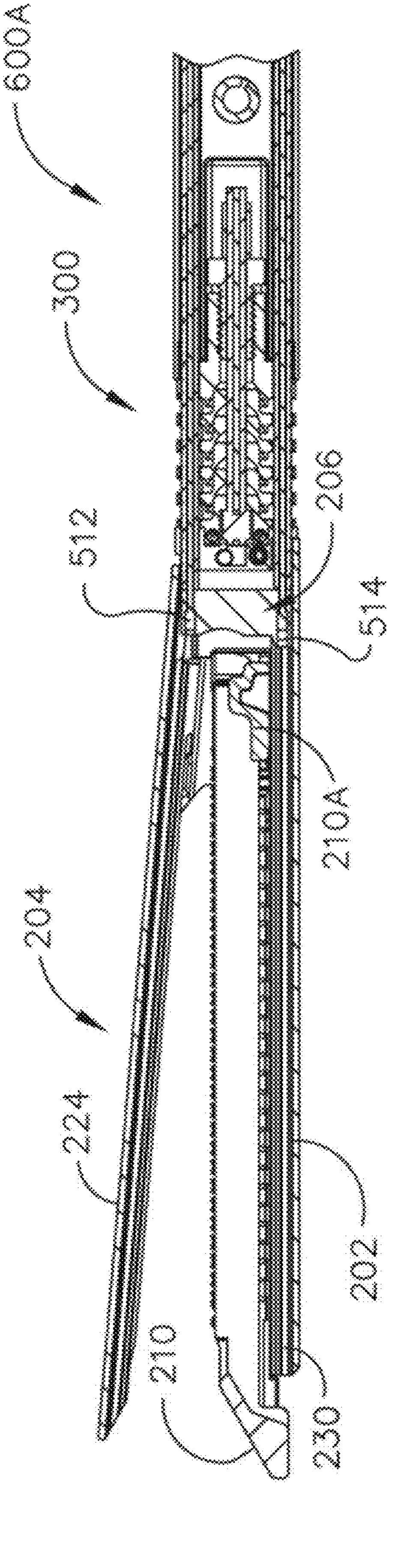
FIG. 5B is a schematic side cross-sectional view of the distal end of the surgical instrument, depicting the anvil in a grasping position with the knife partially advanced, in accordance with the disclosed technology.
Figure 5C:
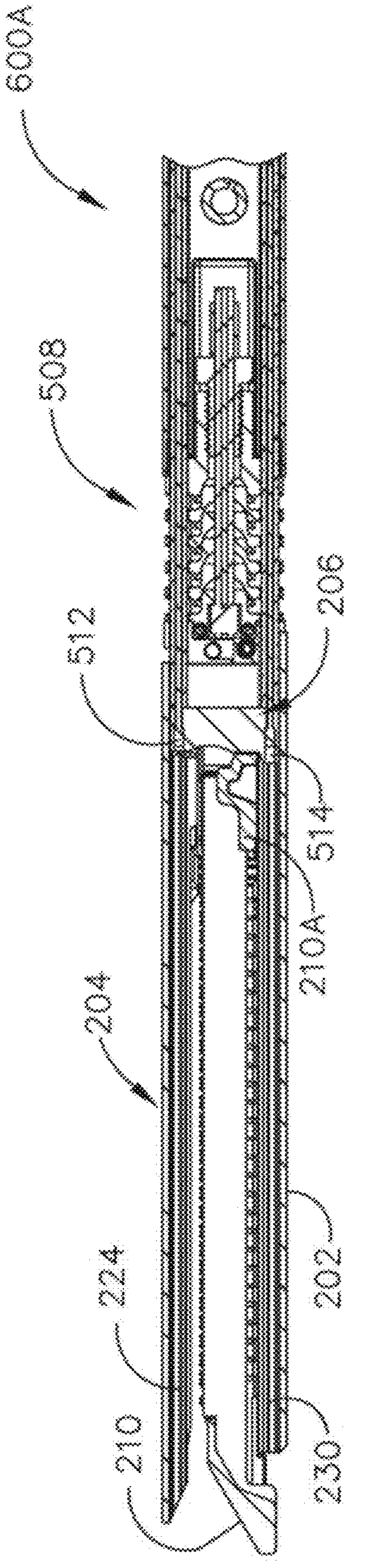
FIG. 5C is a schematic side cross-sectional view of the distal end of the surgical instrument, depicting the anvil in a clamping position with the knife partially advanced, in accordance with the disclosed technology.
Figure 5D:
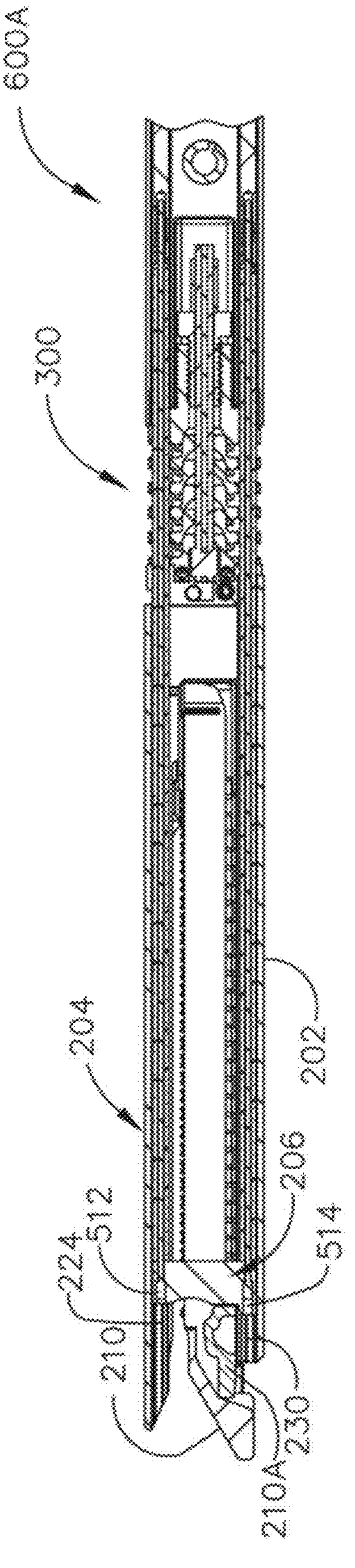
FIG. 5D is a schematic side cross-sectional view of the distal end of the surgical instrument, depicting the anvil in the clamping position with the knife fully advanced, in accordance with the disclosed technology.

Making particular reference to FIG. 4, the lower knife channel 230 includes a centrally disposed cylindrical lower knife channel portion 232 and at least one lateral lower knife channel wing 234 that extends away from the lower knife channel portion 232. While the term 'cylindrical' is used, the channel portion 232 need not resemble a perfect cylinder. Other arrangements of staple cavities and staples may be possible. For example, in some embodiments, a lower knife channel 230 can be defined in the jaw 202.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions indirectly by the sled 236. More specifically, the knife sled 236 is movable between a proximal position adjacent the proximal end and a distal position adjacent the distal end. A portion of the knife sled 236 (e.g., see FIGS. 5C-5D) engages a cartridge sled 210A that slides under the drivers and lifts the drivers, and the staples supported thereon, toward the anvil 204. It is desirable for the knife 206 to be positioned at least partially proximal to the ramped surfaces such that the staples are in the second, or fired, position (i.e., ejected) ahead of the knife 206.

Further to the above, the sled 236 is moved distally and proximally by a firing rod 502. The firing rod 502 is configured to apply an indirect force to the sled 236, via push coils 508, 510 that directly engage the sled 236 (discussed in greater detail below) and push the sled 236 toward the distal end of the end effector 200. As the firing rod 502 is advanced distally, sled 236 rides in the lower knife channel 230 and the upper knife channel 224. At the onset of travel, the upper knife tab 238 rides along the anvil ramp surface 216. Specifically, as particularly seen in the sequence of FIGS. 5A-5D, movement of the sled 236 distally causes the upper knife tab ramped surface 242A to slide along the anvil ramp surface 216. This movement first urges the anvil 204 closed to a position (e.g., FIG. 5B) where a compressive force is applied to the tissue sufficient to grasp it (referred to as the grasping position). Continued movement of the sled

236 up the ramp surface 216 (e.g., see FIG. 5C) results in a compressive force being applied to the tissue (referred to as the clamping position). As the anvil ramp surface 216 transitions to its substantially horizontally angled surface 218 (e.g., see FIG. 5D), the upper knife tab 238 can slide within the upper knife channel 224 to drive the stapling and transection of the tissue.

Figure 6:
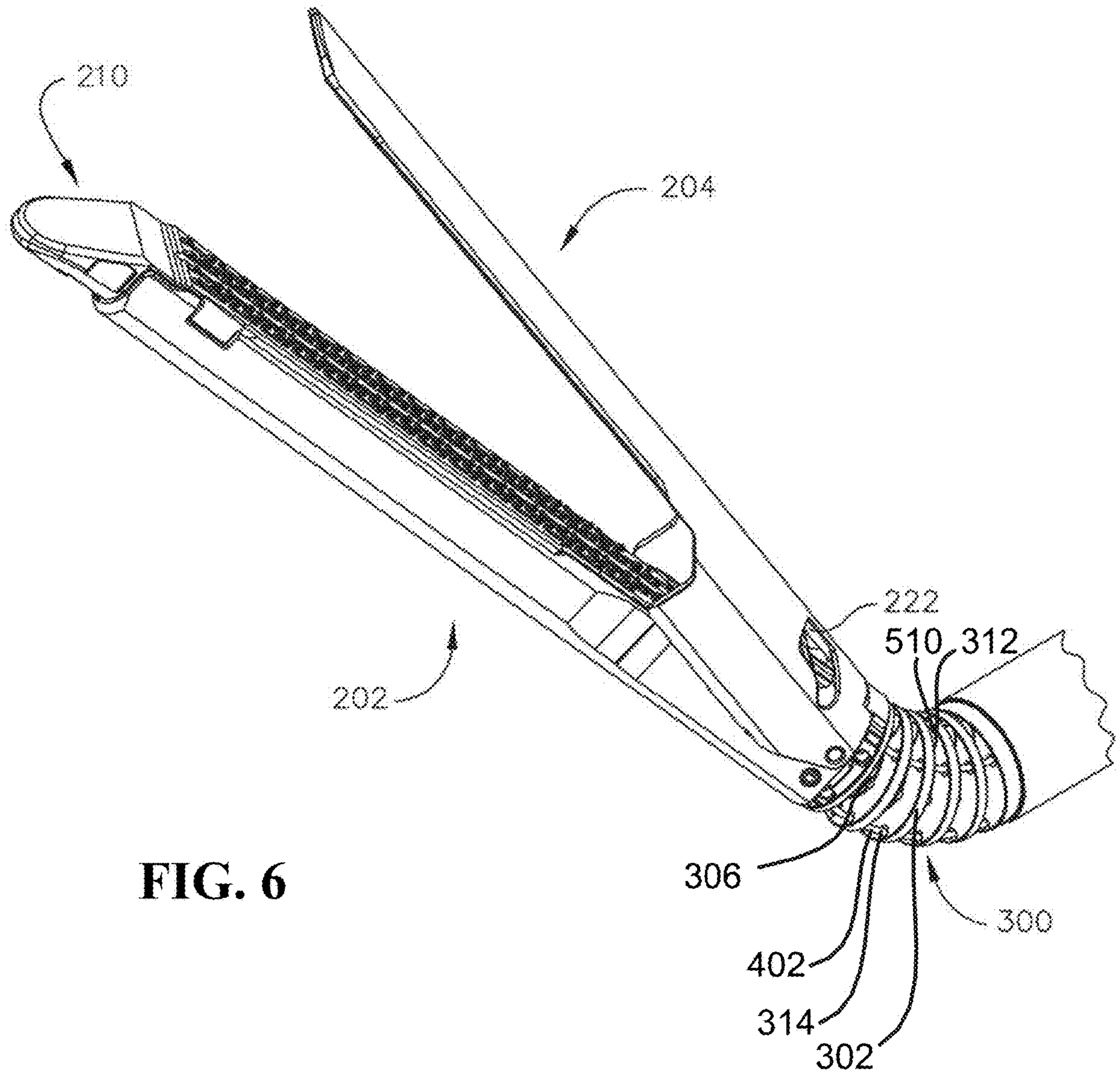
FIG. 6 is a schematic perspective detail view of the distal end of the surgical instrument, depicting the end effector pivoted vertically and laterally with the anvil open, in accordance with the disclosed technology.

Referring to FIG. 6, the end effector 200 can be configured to be oriented in various positions via an articulation joint 300 that comprises a plurality of concentric discs 302 and a center beam assembly 306. Each concentric disc 302 further includes a concentric central opening positioned around the center beam assembly 306. The concentric discs 302 are nestably stacked on the center beam assembly 306 such that adjacent concentric discs 302 interface with one another. The distal end of the center beam assembly 306 couples to the plurality of concentric discs 302 to a proximal end of the end effector 200 of the surgical instrument 1000.

Each concentric disc 302 includes a first push coil opening 312A configured to receive a first push coil 508 therethrough and a second push coil opening 312B configured to receive a second push coil 510 therethrough, and a plurality of articulation cable openings 314 configured to receive a respective articulation cable 402, 404, 406, 408 (e.g., a first articulation cable 402, a second articulation cable 404, a third articulation cable 406, and a fourth articulation cable 408) therethrough. In some embodiments, three articulation cable openings 314 are provided to correspond to three articulation cables 402, 404, 406, while in other embodiments, four articulation cable openings 314 are provided to correspond to four articulation cables 402, 404, 406, 408.

The above-described articulation joint 300 forms a portion of the cable articulation subsystem 400 which allows for precise 360-degree movement of the end effector 200 about the articulation joint 300 with at least two degrees of freedom. In some embodiments, and dictated by the roll subsystem 600 as well as a need to limit the amount of wrap of the articulation cables 402, 404, 406, 408, the articulation joint is permitted about 320 degrees of roll within the overall system.

Each articulation cable 402, 404, 406, 408 includes a stainless-steel material with clockwise braiding and counterclockwise braiding that prevent unwinding thereof. In other embodiments, other materials may be employed, such as polymer yarns and/or filaments, various metal cables (e.g., tungsten), and combinations thereof. Each articulation cable is discretely manipulable to cause rotation of the articulation joint 300 and end effector 200 about at least one of a pitch axis PA and a yaw axis YA.

In some embodiments, three articulation cables may be provided rather than the four cables 402, 404, 406, 408 depicted herein. However, four articulation cables 402, 404, 406, 408 circumferentially spaced approximately ninety degrees from one another (as shown) provides load splitting. Additionally, in alternative embodiments, three and four articulation cable configurations may be spaced non-symmetrically relative to one another.

Figure 13A:
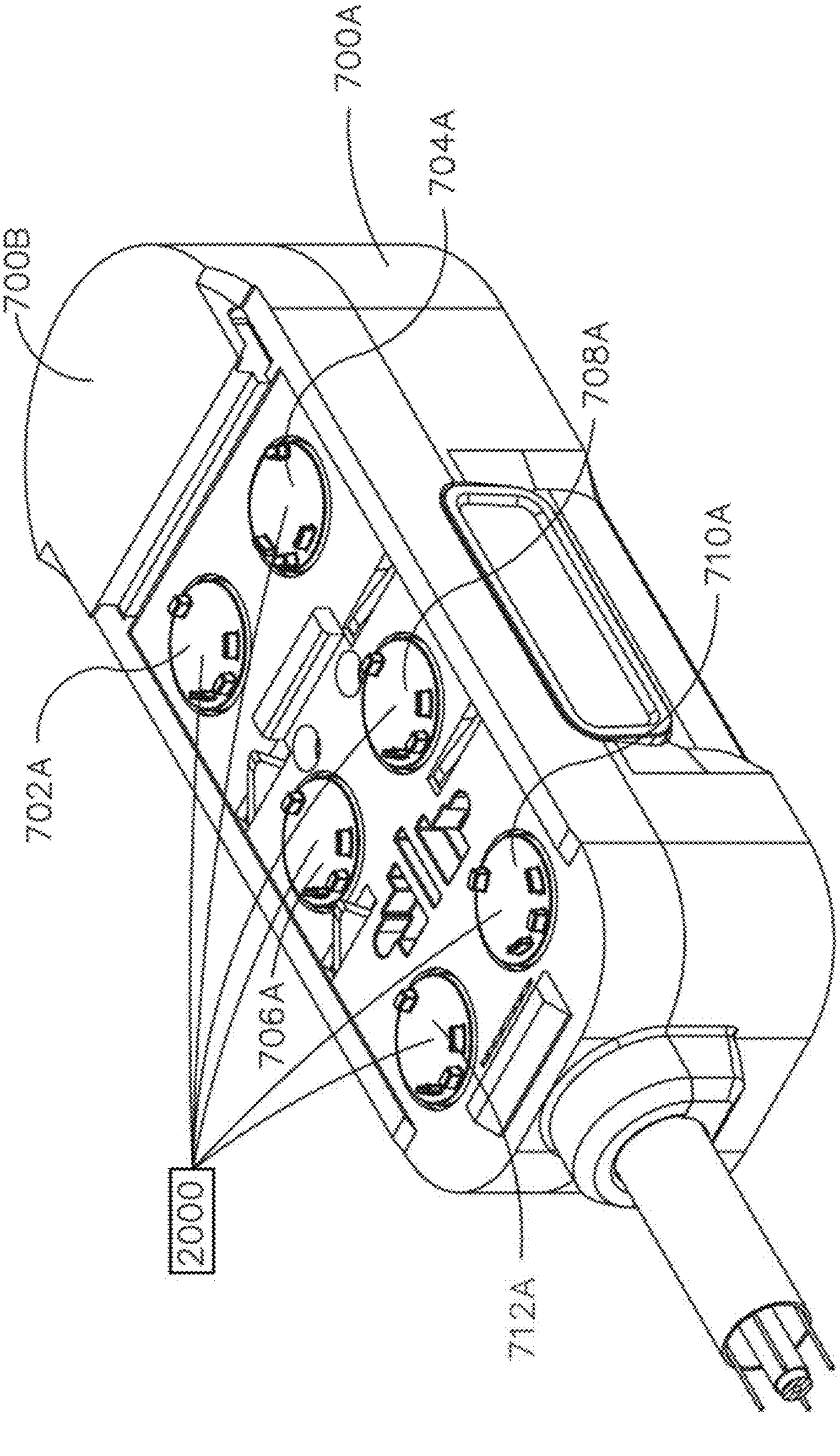
FIG. 13A is a schematic detail view of one side of a housing, depicting rotational pucks that engage a robotic platform, in accordance with the disclosed technology.

The shaft assembly 600A and housing 700 also form portions of the cable articulation subsystem 400. More specifically, each articulation cable 402, 404, 406, 408 extends from the articulation joint 300 and through the shaft assembly 600A to the housing 700. The proximal end 402B, 404B, 406B, 408B of each articulation cable (402, 404, 406) is movably mounted in the housing 700 which causes the above-mentioned rotation of the articulation joint 300 and end effector 200. As shown in FIG. 13A, the housing 700 includes articulation puck assemblies 702, 704, 706, 708 with rotatable capstans 702B, 704B, 706B, 708B, discussed in greater detail below, about which corresponding proximal ends 402B, 404B, 406B, 408B of the articulation cables 402, 404, 406, 408 are windably mounted thereto. The capstans 702B, 704B, 706B, 708B can be vertically offset from one another (e.g., capstan 702B and capstan 704B can be located proximal one portion (e.g., upper shroud 700A) of the housing 700, and capstan 706B and capstan 708B can be located proximal another portion (e.g., lower frame 700B) of the housing 700.

The articulation cables 402, 404, 406, 408 are routed through the shaft assembly 600A such that they are disposed between the outer shaft 602 and the inner shaft 604, with the articulation cables 402, 404, 406, 408 being able to partially wind therearound without becoming tangled. The inner shaft 604 also prevents the articulation cables 402, 404, 406, 408 from interfering with other components running down the center of the instrument 1000 (through the inner shaft 604).

The articulation cables 402, 404, 406, 408 are routed and coupled to the end effector 200 via the articulation joint 300 such that movement thereof in a proximal direction (via winding about the capstans 702B, 704B, 706B, 708B) causes the end effector 200 to pivot in a predetermined manner about the articulation joint 300. For example, actuation of the first articulation cable 402 in the proximal direction causes rotation of the end effector 200 upwards and to the left, actuation of the second articulation cable 404 in the proximal direction causes rotation of the end effector 200 upwards and to the right, actuation of the third articulation cable 406 in the proximal direction causes rotation of the end effector 200 downwards and to the left, and actuation of the fourth articulation cable 408 in the proximal direction causes rotation of the end effector 200 downwards and to the right. Similarly, movement of two articulation cables simultaneously will result in blended movement of the end effector 200. By way of example, movement of both the first articulation cable 402 and the second articulation cable 404 at the same rate causes only upwards pivoting of the end effector 200 (i.e., there is little to no horizontal component to the rotation). As will be appreciated by those skilled in the art, this configuration provides for the above-mentioned precise 360-degree movement of the end effector about the articulation joint 300 with at least two degrees of freedom and about 320 degrees of roll.

Referring primarily to FIGS. 2, 5A-5D, 9A-9D, 7 and 12, the knife firing subsystem 500 includes the aforementioned knife 206, the aforementioned sled 236, a firing rod 502 that drives the knife 206 and/or sled 236, a first push rod 504, and a second push rod 506. The firing rod 502 includes a firing rod rack 530 and is driven by a firing puck assembly 712, which is described in greater detail below. The first push rod 504 has a first push rod distal end 504A coupled to the sled 236 and a first push rod proximal end 504B coupled to the firing rod 502. Similarly, the second push rod has a second push rod distal end 506A coupled to the sled 236 and a second push rod proximal end 506B coupled to the firing rod 502. The distal ends 504A, 506A are coupled to respective upper and lower portions of the sled 236 (e.g., the upper knife tab 238 and the lower knife tab 246), which enables the knife 206 to be pushed evenly at its ends. In some embodiments, the proximal ends 504B, 506B of the push rods 504, 506 are coupled to the firing rod via a differential 520, which is discussed in greater detail below.

The knife firing subsystem 500 is configured in a manner to enable articulation of the end effector 200 while still enabling proper functionality of the knife 206. To that end, the first push rod 504 includes a first flexible section 508 and the second push rod 506 comprises a second flexible section 510. As particularly shown in FIGS. 9-11, the flexible sections 508, 510 route through the articulation joint 300 via the respective push coil openings 312A, 312B and the push rods 504, 506 engage the respective tab openings 244, 252 in the sled 236. More specifically, the first flexible section 508 includes a first push coil 508 and a first center cable 512 extends through the first push coil 508 to engage the sled 236 via a barrel crimp, and the second flexible section 510 includes a second push coil 510 and a second center cable 514 extends through the second push coil 510 to engage the sled 236 via a barrel crimp. The push coils 508, 510 provide the rods 504, 506 sufficient stability to deliver a firing force to the knife 206, while not being too stiff that would prevent articulation at the joint 300. The cables 512, 514, which are engaged with the sled 236 as discussed above (see, e.g., FIG. 5A), prevent the coils 508, 510 from stretching and/or elongating and serve as retraction cables when the rods 504, 506 are retracted towards the proximal end of the surgical instrument 1000.

Figure 9:
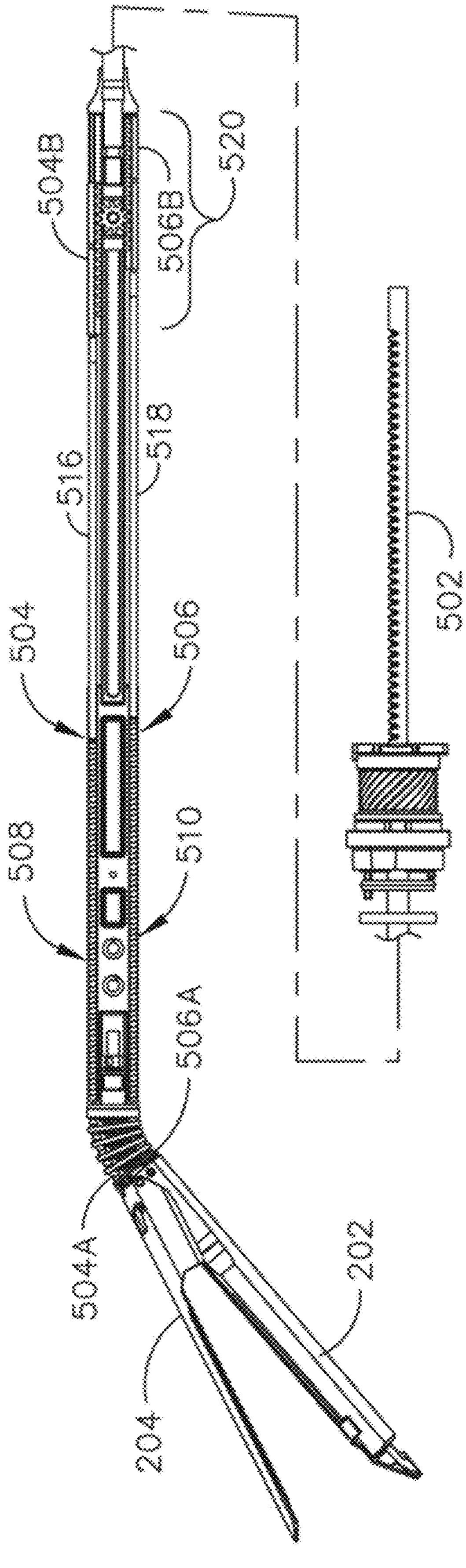
FIG. 9 is a schematic side view of the firing subsystem, depicting the end effector pivoted vertically downwards and the anvil in the open position, in accordance with the disclosed technology.
Figure 10:
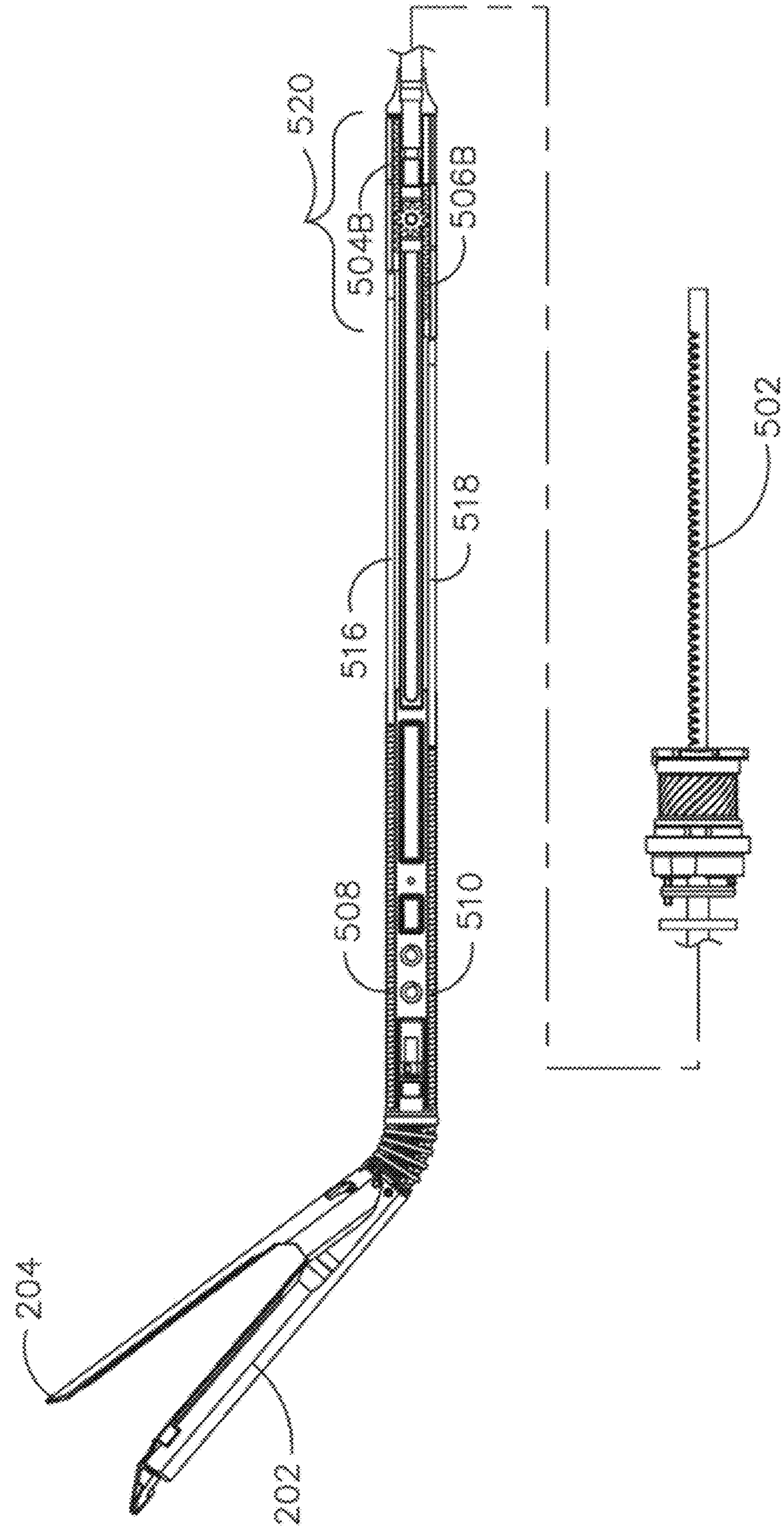
FIG. 10 is a schematic side view of the firing subsystem, depicting the end effector pivoted vertically upwards and the anvil in the open position, in accordance with the disclosed technology.
Figure 11:
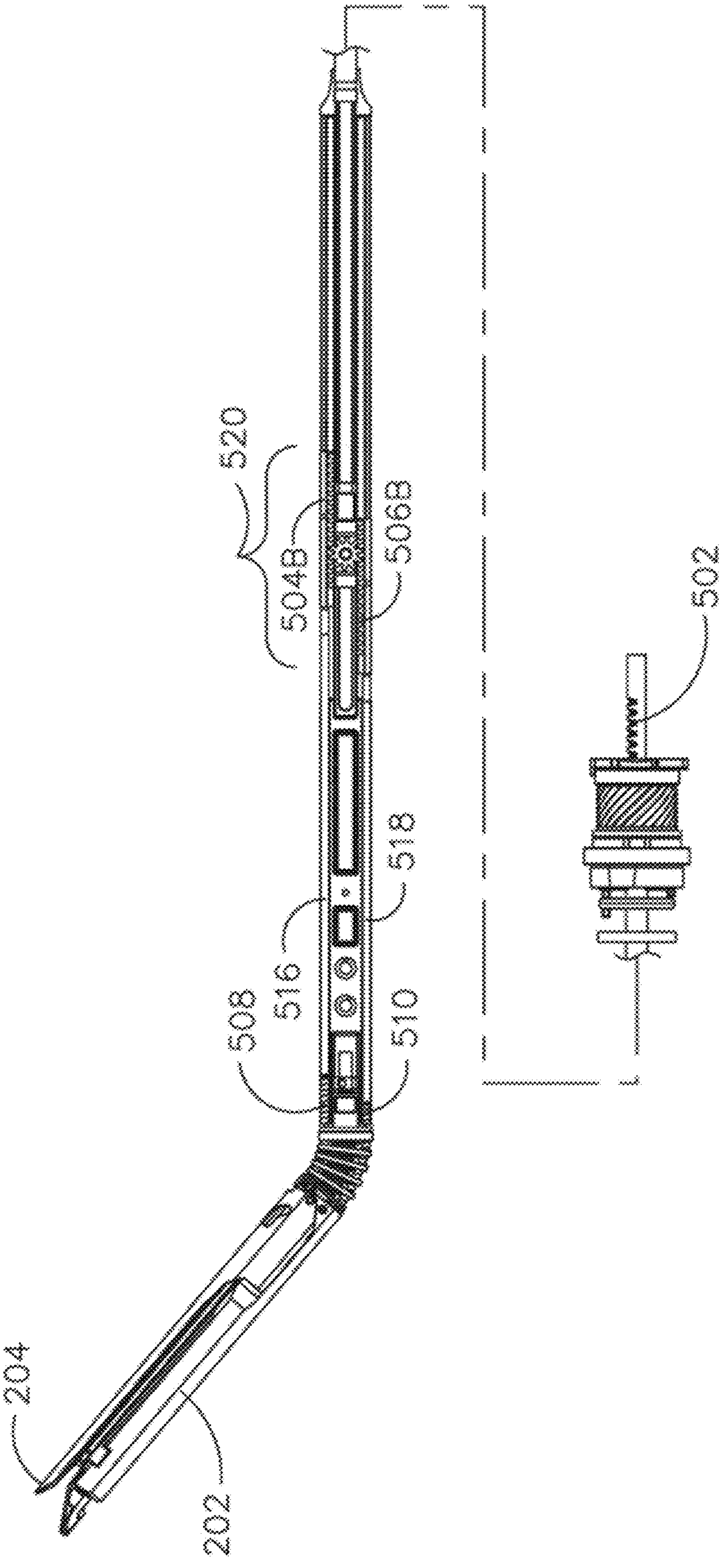
FIG. 11 is a schematic side view of the firing subsystem, depicting the end effector pivoted vertically upwards and the anvil in the clamping position and the knife fully advanced, in accordance with the disclosed technology.

With continued reference to FIGS. 9-11, the entirety of the push rods 504, 506 do not bend and/or extend through the articulation joint 300, in use, and therefore does not need to be flexible. Accordingly, a proximal section of each push rod 504, 506 includes a rigid rod 516, 518. As used, the term 'rigid' refers to a structure less flexible than the described push coils 508, 510 and cables 512, 514. Specifically, the first push rod 504 includes a first rigid rod 516 coaxial with and coupled to the first push coil 508 and first center cable 512, and the second push rod 506 includes a second rigid rod 518 coaxial with and coupled to the second push coil 510 and second center cable 514.

Further to the above, depending on the manner in which the end effector 200 is pivoted about the articulation joint 300, the bend radius for the first push coil 508 and the second push coil 510 can differ. For example, in the configuration shown in FIG. 10 (i.e., when the end effector 200 is pivoted upwards), the first push coil 508 has a smaller bend radius than the second push coil 510, leading to a greater amount of the second push coil 510 extending through the articulation joint 300 than the first push coil 508. A differential 520 is provided to account for these differing bend radii, as well as to balance any difference in loading, ensuring an even split of the firing force being delivered to the push rods 504, 506.

More specifically, the differential 520 couples the first push rod proximal end 504B and the second push rod proximal end 506B to the firing rod 502, and the differential 520 permits relative axial movement between the first push rod 504 and the second push rod 506 (e.g., as depicted in FIGS. 9, 10 and 14-16). The differential 520 includes a first rack 522 coupled to the first push rod 504, a second rack 524 coupled to the second push rod 506, a carrier 526 rotatably coupled to the firing rod 502, and a pinion 528 rotatably mounted on the carrier 526 and meshed with the first rack 522 and the second rack 524.

Further to the above, as particularly exemplified in FIGS. 9 and 10, the first rack 522 and the second rack 524 are movable in opposing axial directions relative to one another in response to rotation of the sled 236 about the pitch axis PA to account for the aforementioned differing bend radii of the push coils 508, 510.

Further, as shown in FIG. 11, the first rack 522 and the second rack 524 are each movable in the same axial direction (e.g., a first axial direction) in response to movement of the firing rod 502 in the first axial direction with a firing force. As discussed above, this firing force is delivered through the push coils 508, 510 to the knife 206, which closes the anvil 204 to a grasping position and/or a clamping position. As shown in the sequence depicted in FIGS. 9A-9D, movement of the push coils 508, 510 distally results in them riding in the central upper knife channel portion 226 of the upper knife channel 224 and the central lower knife channel portion 232 of the lower knife channel 230, respectively. Further movement of the firing rod 502 in the first axial direction continues movement of the knife 206 to fire the staples and transect tissue, as discussed above. Retraction of the knife 206 and opening of the anvil is achieved by moving the firing rod 502 in an opposite, second direction. As demonstrated in FIGS. 10 and 11, due to the independent cable articulation system 400 and knife firing subsystem 500, the knife 206 and sled 236 can be oriented and translate non-parallel to an orientation and movement of the firing rod 502.

Figure 14:
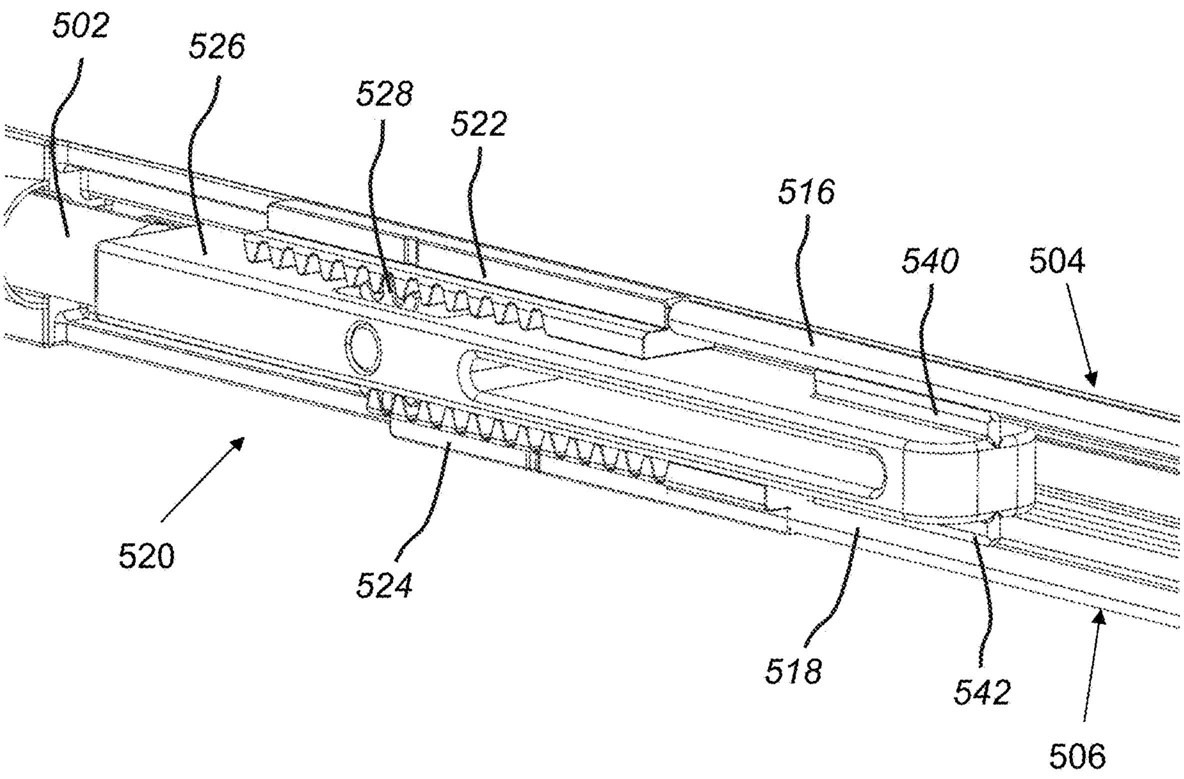
FIG. 14 is a schematic view of a differential of the firing subsystem, in accordance with the disclosed technology.
Figure 15:
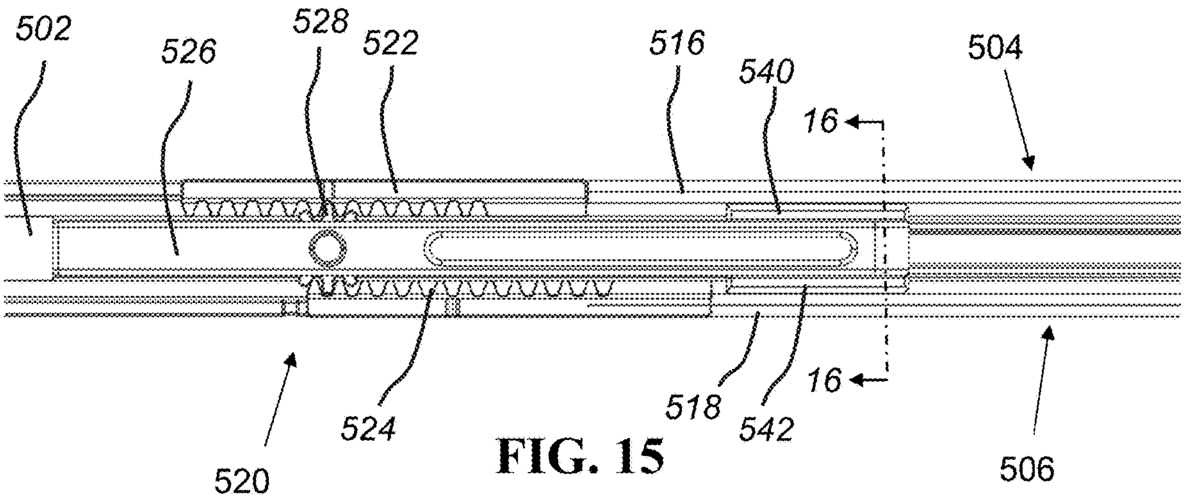
FIG. 15 is a schematic side view of a differential of the firing subsystem, in accordance with the disclosed technology.
Figure 16:
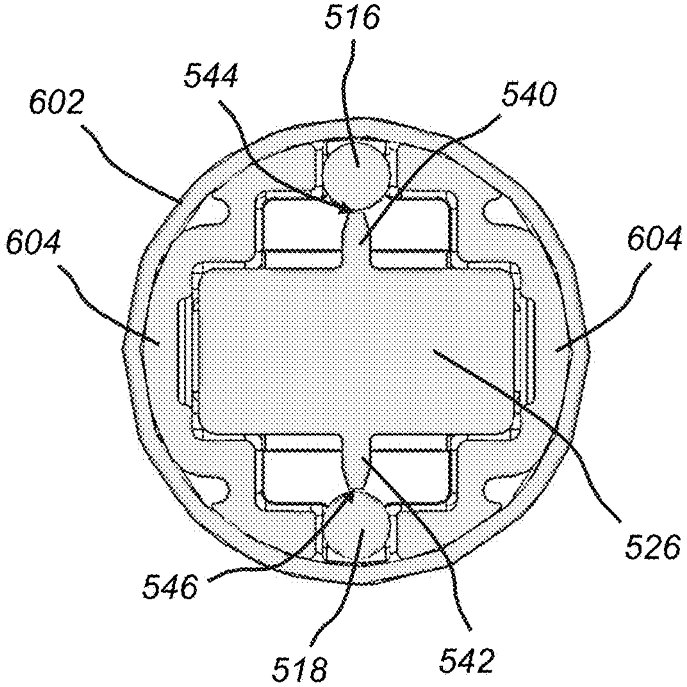
FIG. 16 is a cross-sectional view of the differential of the firing subsystem, in accordance with the disclosed technology.

As will be appreciated, as the knife 206 is pushed distally by the first rigid rod 516, the second rigid rod 518, and the push coils 508, 510, the force necessary to cut the tissue can be great depending on the type and amount of tissue being cut. As shown in FIGS. 14-16, to help ensure the first rigid rod 516 and the second rigid rod 518 are prevented from buckling due to the force necessary for cutting, the carrier 526 can include a first fin 540 and a second fin 542 that each extend transversely outward from the carrier 526 away from the longitudinal axis and are configured to support the push rods 504, 506. The fins 540, 542, for example, can be positioned along the carrier 526 at a distal end of the carrier 526 and can be positioned to best support the push rods 504, 506 from buckling. Alternatively, the fins 540, 542 can extend along the entire length of the carrier 526. That is, the fins 540, 542 are either positioned far enough down the length of the push rods 504, 506, or extend along the length of the push rods 504, 506, such that the buckling strength of the push rods 504, 506 is increased at least by 70 lbs. In other examples, the buckling strength of the push rods 504, 506 can be increased at least by 100 lbs. In other words, because the fins 540, 542 are configured to prevent the push rods 504, 506 from bending as they are pushed distally, the fins 540, 542 significantly increase the strength of the push rods 504, 506 and reduce the likelihood that they buckle. Stated otherwise, the fins 540, 542 reduce the buckling length of the push rods 504, 506 by approximately one inch, thereby increasing the overall force that the push rods 504, 506 are able to withstand.

Because the fins 540, 542 are positioned on the carrier 526, there is no relative motion between the push rods 504, 506 and the fins 540, 542 during the firing phase. That is, both the carrier 526 and the push rods 504, 506 translate at the same speed. This eliminates any occurrence of drag due to frictional losses between the push rods 504, 506 and the fins 540, 542. Alternatively, or in addition, to help ensure the force necessary to drive the push rods 504, 506 distally is not significantly increased due to frictional forces between the push rods 504, 506 and the fins 540, 542 in a configuration where the push rods 504, 506 happen to slide at least partially with respect to the fins 540, 542, the fins 540, 542 can be configured such that there is a small gap between the fins 540, 542 and the push rods 504, 506. The gap 544 can be sized such that the push rods 504, 506 contact the fins 540, 542 and are further prevented from bending after the push rods 504, 506 are subjected to a predetermined force.

As shown in FIG. 16, in some examples, the fins 540, 542 can include a recess 546 to at least partially receive the push rods 504, 506 and help ensure the push rods 504, 506 remain aligned with the longitudinal axis. Alternatively, the fins

540, 542 can each converge toward a point at the interface between the push rods 504, 506 and the fins 540, 542 to reduce any frictional forces between the push rods 504, 506 and the fins 540, 542.

Figure 17A:
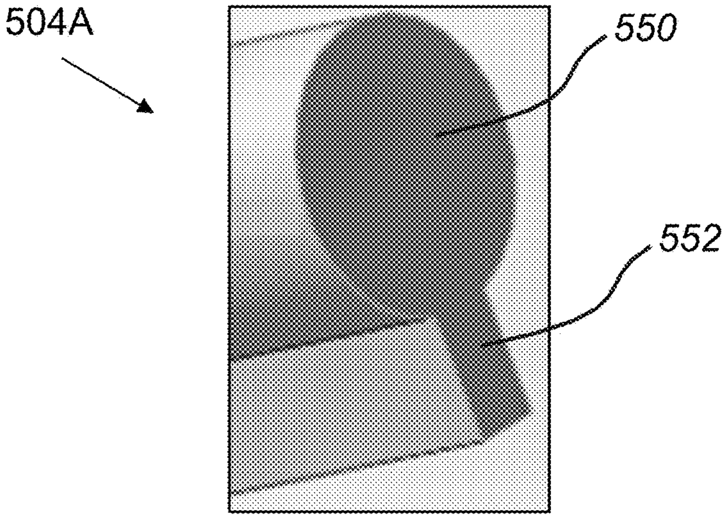
FIGS. 17A-17C illustrate isometric end views of alternative pushrods having various features configured to reduce buckling, in accordance with the disclosed technology.
Figure 17B:
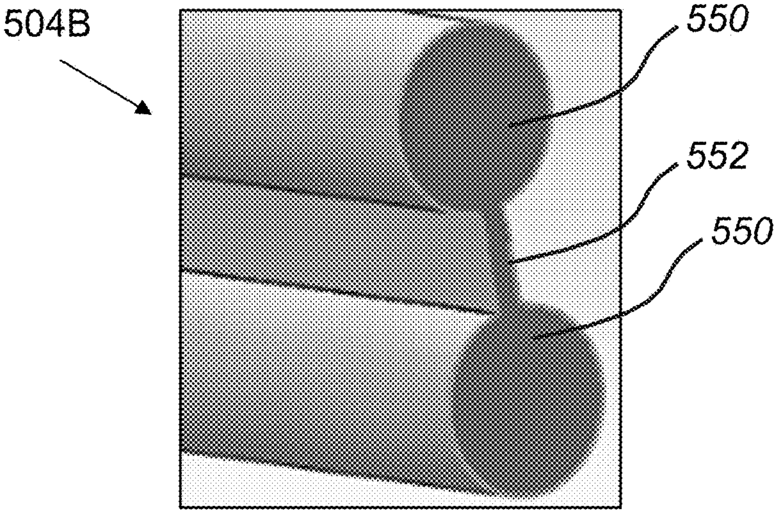
Figure 17C:
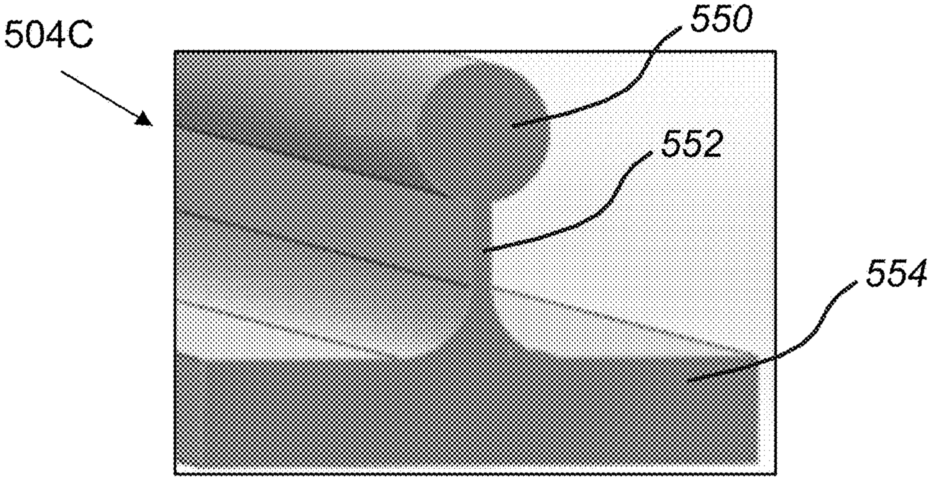

Alternatively, or in addition, the push rods 504, 506 can be further configured to resist buckling. That is, the push rods 504, 506 can be configured with a cross-sectional profile or other features known to help reduce buckling of the push rods 504, 506. For example, the pushrods 504, 506 can include features similar to an I-beam that help to reduce buckling, such as those shown and described in relation to FIGS. 17A-17C. FIGS. 17A-17C illustrate isometric end views of alternative pushrods 504 having varying features to reduce buckling. Although shown and described in relation to the first pushrod 504, it will be appreciated that the same concepts can be applied to the second pushrod 506. As shown in FIG. 17A, a pushrod 504A can include a rod 550 and a web 552 extending outwardly from the rod 550. As another example, as shown in FIG. 17B, a pushrod 504B can include two rods 550 joined together by a web 552. As yet another example, a pushrod 504C can include a rod 550 and a flange 554 that are joined together by a web 552. Any of the pushrods 504A, 504B, 504C just described can be oriented or otherwise arranged in such a way that the pushrod 504A, 504B, 504C is best able to resist buckling forces. In this way, the knife firing subsystem 500 can be configured to apply an increased driving force to the knife 206 without causing the pushrod 504 to buckle.

In order to permit roll of the outer shaft 602, the differential 520 is mounted in the shaft assembly 600A and is coupled to the firing rod 502 such that it is rotatable about a roll axis RA. As a result, the carrier 526 is axially constrained relative to the firing rod 502 and freely rotatable relative thereto.

Figure 8:
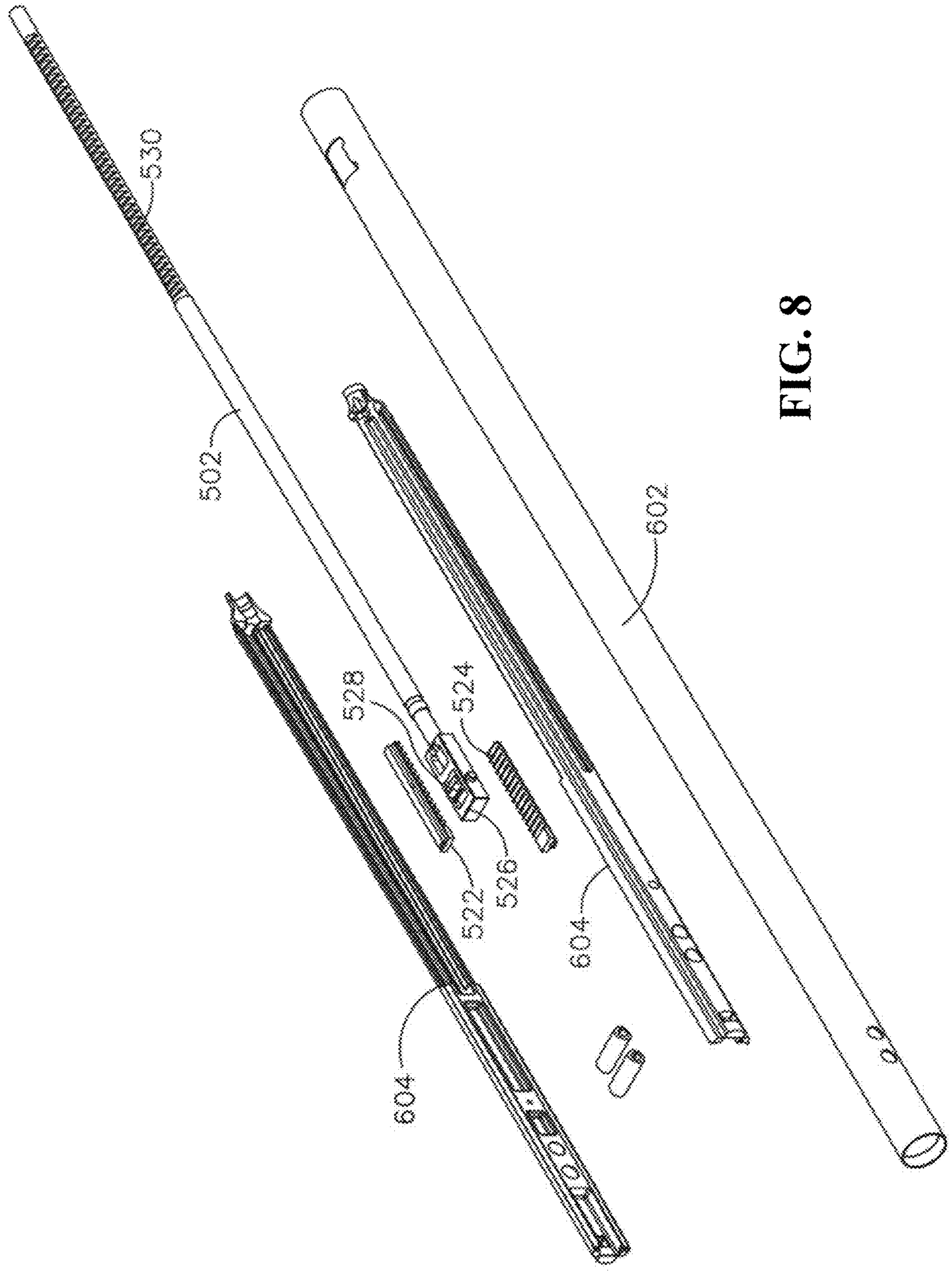
FIG. 8 is a schematic perspective view of a shaft assembly, a differential, and a firing rod of the surgical instrument, in accordance with the disclosed technology.

The roll subsystem includes the above-mentioned shaft assembly 600A, rotation joint 606, shaft roll puck assembly 710. As discussed in the foregoing paragraph, the rotatable nature of the differential 520 is also a feature of the roll subsystem 600. The shaft assembly 600A includes the previously discussed rotatable outer shaft 602 and the inner shaft 604. As shown in the exploded view of FIG. 8, the inner shaft 604 can be split clamshell in design that couple to one another and houses certain components of the surgical instrument 1000, such as the differential 520 and a distal portion of the firing rod 502. Additionally, the clamshell inner shaft 604 can provide support for certain portions of the push coils 508, 510. The inner shaft 604 is fixedly coupled to the outer shaft 602 such that they are rotationally linked. The outer shaft 602 is coupled to the housing via the rotation joint 606, which may include one or more bearings. The bearings engage the housing 700 and permit relative rotation between the outer shaft 604 and the housing 700 upon actuation of the shaft roll puck assembly. One or both of the shafts 602, 604 are provided with various channels for the cables 402, 404, 406, 408, push rods 504, 506, differential 520, and the like to ride in. Further, a lug is rotationally fixed to the outer shaft and is configured to bottom out with a cavity on the housing to indicate when the outer shaft 602 is in a home position.

Figure 12:
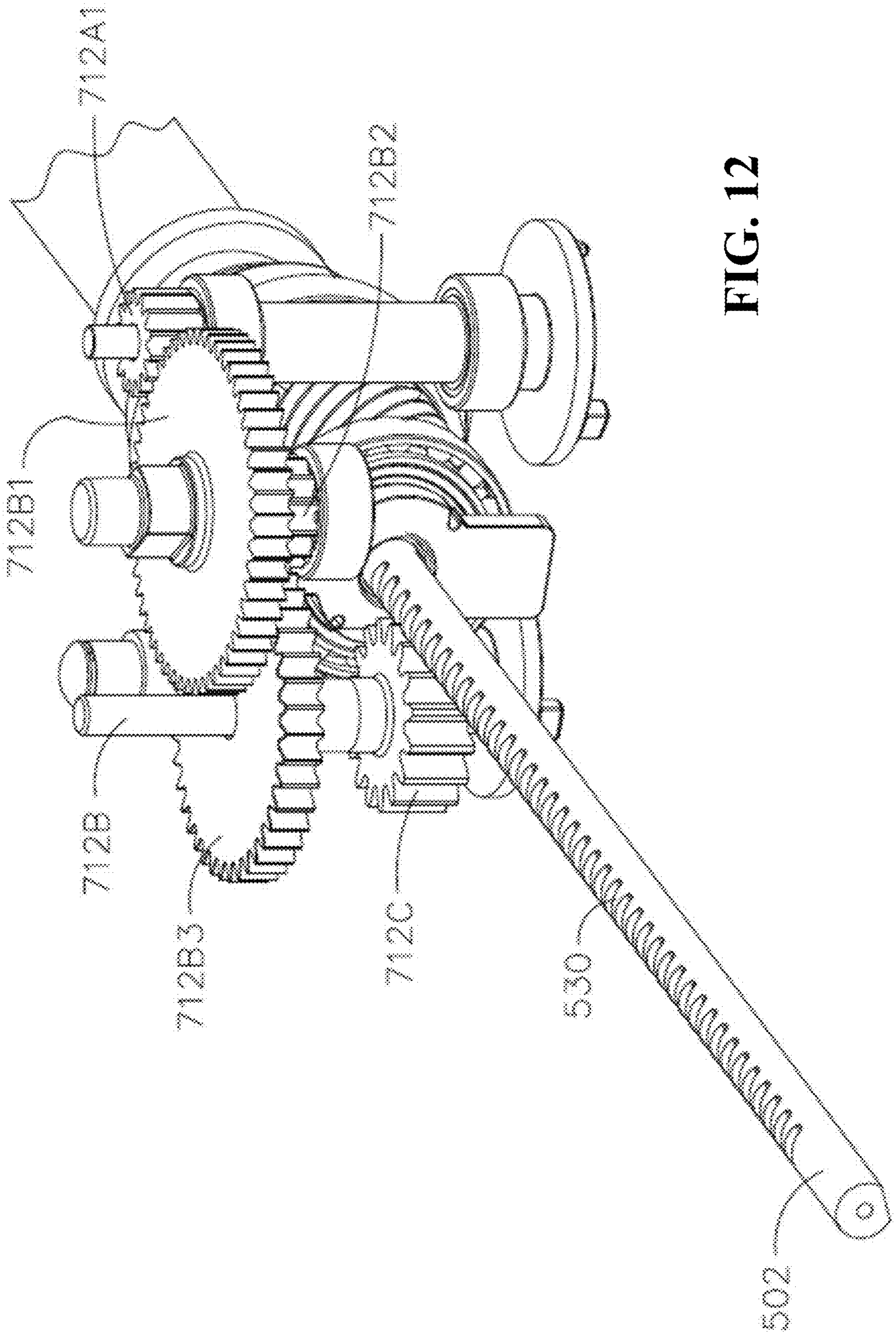
FIG. 12 is a schematic detail view of the proximal end of the surgical instrument, depicting portions of the knife firing subsystem, in accordance with the disclosed technology.

As shown in FIG. 12, the firing puck assembly includes a firing puck 712A, a drive gear 712A1, a geartrain 712B, and a driven gear or pinion 712C. The firing puck 712A is provided on an outer face of the lower frame 700B, is integral with a sixth pivot pin 736, and directly engages the robotic platform 2000. The drive gear 712A1 directly rotates with the firing puck 712A. The geartrain 712B is rotatable with the firing puck 712A and the drive gear 712A1. In some embodiments, the geartrain 712B includes a first idler gear 712B1 meshed with the drive gear 712A1, a second idler gear 712B2 coaxial with and rotationally affixed to the first idler gear 712B1, and a third idler gear 712B3 meshed with the second idler gear 712B2. The pinion 712C is coaxial with and rotationally affixed to the third idler gear 712B3. Further, the pinion 712C meshes with the rack 530 of the firing rod 502 to effect translational movement thereof (to fire and retract the knife 206, as discussed above).

In use, and for example, rotation of the firing puck 712A by the robotic platform 2000 causes rotation of the drive gear 712A1, which in turn drives the geartrain 712B to rotate the pinion 712C. Depending on the direction of rotation of the firing puck 712A, the firing rod 502 is either moved in a distal direction (i.e., towards the end effector 200) to close the anvil 204 and/or fire the knife 206 or a proximal direction (i.e., towards a rear of the housing 700) to retract the knife 206 and/or open the anvil 204.

Figure 13B:
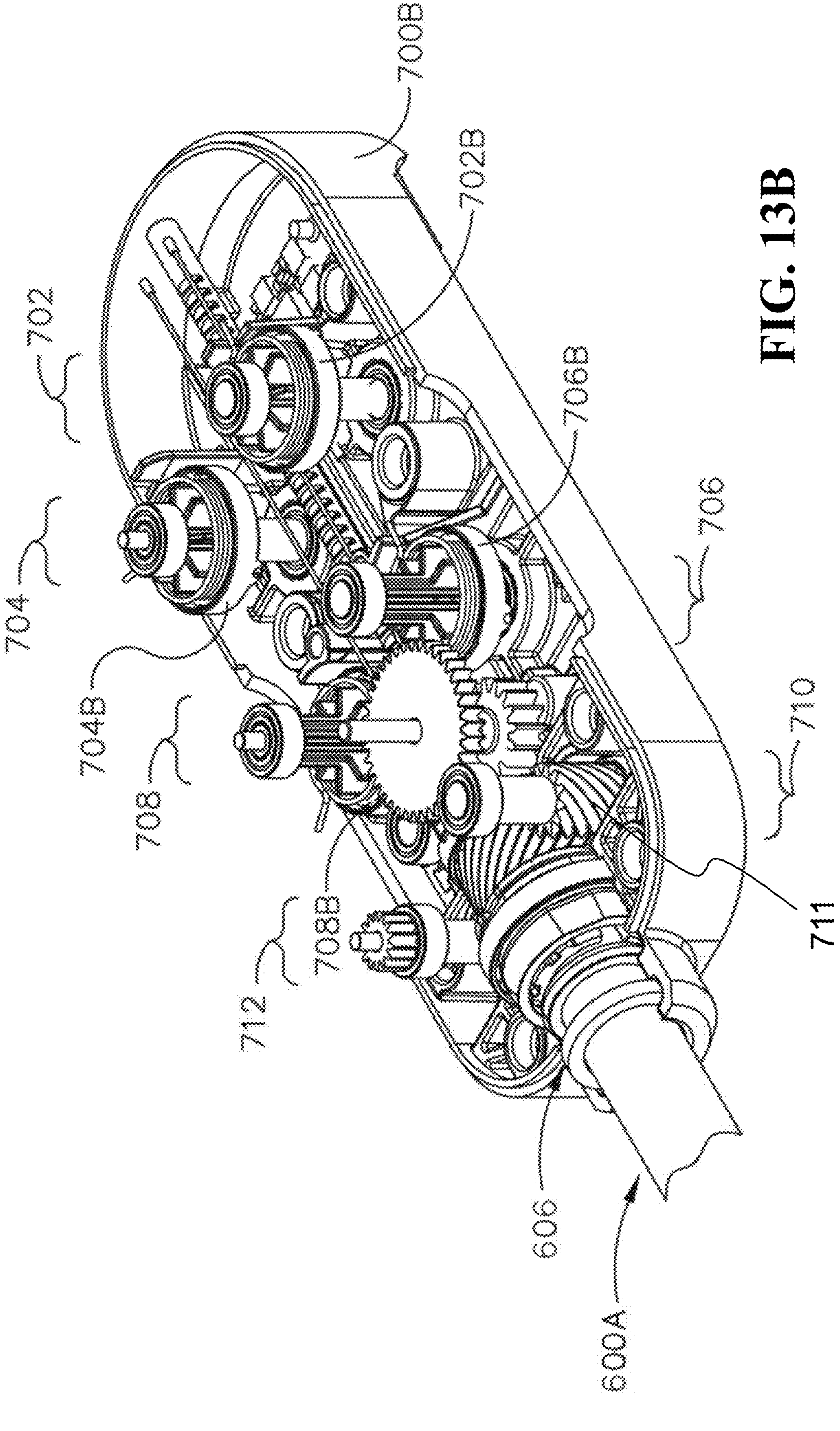
FIG. 13B is a schematic perspective view of the housing with the upper shroud and middle frame thereof removed, in accordance with the disclosed technology.

As shown in FIGS. 13A and 13B, the surgical instrument 1000 further comprises a housing 700 and a shaft assembly 600A extending from the housing 700. The housing is configured to engage a robotic platform 2000. In some embodiments, the housing 700 may be configured as a handle (e.g., it may comprise a grip for a clinician). The shaft assembly 600A comprises a rotatable outer shaft 602 and an inner shaft 604, the outer shaft 602 being rotatably mounted to the housing about a rotation joint 606 (which may include one or more bearings). The inner shaft 604 is rotationally fixed to the outer shaft 602 and is configured such that articulation cables 402, 404, 406, 408, discussed in greater detail below, can be partially wound therearound without becoming tangled. As discussed in greater detail below, the housing 700 further comprises (1) a firing puck assembly 712 as part of the knife firing subsystem 500 operable to close the end effector 200, fire staples, and transect tissue, (2) a set of articulation puck assemblies 702, 704, 706, 708 as part of the articulation subsystem 400 operable to articulate the end effector 200 relative to the shaft assembly 600A, and (3) a shaft roll puck assembly 710 as part of the roll subsystem 600 configured to roll the outer shaft 602.

The housing 700 is configured to engage a robotic platform 2000 controlled by a clinician. To control the aforementioned subsystems 400, 500, 600, respective proximal mechanisms are provided that interface with the robotic platform. More specifically, a housing outer shell, which includes an upper shroud 700A, a lower frame 700B, and a middle frame 700C, houses at least (1) a plurality of articulation puck assemblies 702, 704, 706, 708 for articulation of the end effector 200, (2) a shaft roll puck assembly 710 for rolling the outer shaft 602, (3) a firing puck assembly for translating the knife 206, and (4) a near field radio-frequency identification (RFID) board 724 that communicates information about the surgical instrument 1000 to the robotic platform 2000.

Further to the above, the housing includes four articulation puck assemblies 702, 704, 706, 708, provided that four articulation cables 402, 404, 406, 408 are employed in the presently described surgical instrument. A first articulation puck assembly 702 is used cooperatively with the first articulation cable 402. Likewise, the second articulation puck assembly 704 is used cooperatively with the second articulation cable 404, the third articulation puck assembly 706 is used cooperatively with the third articulation cable 406, and the fourth articulation puck assembly 708 is used cooperatively with the first articulation cable 408. In use, the first articulation cable 402 winds on and off the first articulation puck assembly 702, the second articulation cable 404 winds on and off the second articulation puck assembly 704, the third articulation cable 406 winds on and off the third articulation puck assembly 706, and the fourth articulation cable 408 winds on and off the first articulation puck assembly 708.

The first articulation puck assembly 702 includes a first articulation puck 702A, a first capstan 702B, and a first torsion spring 702C. The first articulation puck 702A is provided on an outer face of the lower frame 700B and directly engages the robotic platform 2000. The first capstan 702B is coupled to the first articulation puck 702A and winds the first articulation cable 402 therearound. The first capstan 702B is rotationally affixed to a first pivot pin 726 (which is integral with the first articulation puck 702A). The first capstan 702B is biased by a first torsion spring 702C in a retracting direction to maintain a minimum level of tension in the first articulation cable 402, such as while decoupled from the robotic platform 2000. As the first articulation puck assembly 702 does not include any gearing, the diameter of the first capstan 702B is what dictates the mechanical advantage achieved.

In use, and for example, rotation of the first capstan 702B by the robotic platform 2000, via the first articulation puck 702A, in a first direction winds the first articulation cable 402 around the first capstan 702B, which results in the end effector 200 pivoting upwards and to the left about the articulation joint 300. As discussed earlier, this upwards movement of the end effector 200 is compensated for in the knife firing subsystem by the differential 520. Rotation in the opposite direction by the first articulation puck 702A unwinds the first articulation cable 402 to return the end effector 200 to a position substantially coaxial with the shaft assembly 600A (e.g., coaxial with the roll axis RA).

The second articulation puck assembly 704 includes a second articulation puck 704A, a second capstan 704B, and a second torsion spring 704C. The second articulation puck 704A is provided on an outer face of the lower frame 700B and directly engages the robotic platform 2000. The second capstan 704B is coupled to the second articulation puck 704A and winds the second articulation cable 404 therearound. The second capstan 704B is rotationally affixed to a second pivot pin 728 (which is integral with the second articulation puck 704A). The second capstan 704B is biased by a second torsion spring 704C in a retracting direction to maintain a minimum level of tension in the second articulation cable 404. As the second articulation puck assembly 704 does not include any gearing, the diameter of the second capstan 704B is what dictates the mechanical advantage achieved.

In use, and for example, rotation of the second capstan 704B by the robotic platform 2000, via the second articulation puck 704A, in a first direction winds the second articulation cable 404 around the second capstan 704B, which results in the end effector 200 pivoting upwards and to the right about the articulation joint 300. As discussed earlier, this upwards movement of the end effector 200 is compensated for by the differential 520 in the knife firing subsystem. Rotation in the opposite direction by the second articulation puck 704A unwinds the second articulation cable 404 to return the end effector 200 to a position substantially coaxial with the shaft assembly 600A (e.g., coaxial with the roll axis RA).

The third articulation puck assembly 706 includes a third articulation puck 706A, a third capstan 706B, and a third torsion spring 706C. The third articulation puck 706A is provided on an outer face of the lower frame 700B and directly engages the robotic platform 2000. The third capstan 706B is coupled to the third articulation puck 706A and winds the third articulation cable 406 therearound. The third capstan 706B is rotationally affixed to a third pivot pin 730 (which is integral with the third articulation puck 706A). The third capstan 706B is biased by a third torsion spring 706C in a retracting direction to maintain a minimum level of tension in the third articulation cable 406. As the third articulation puck assembly 706 does not include any gearing, the diameter of the third capstan 706B is what dictates the mechanical advantage achieved.

In use, and for example, rotation of the third capstan 706B by the robotic platform 2000, via the third articulation puck 706A, in a first direction winds the third articulation cable 406 around the third capstan 706B, which results in the end effector 200 pivoting downward and to the left about the articulation joint 300. As discussed earlier, this downwards movement of the end effector 200 is compensated for in the knife firing subsystem by the differential 520. Rotation in the opposite direction by the third articulation puck 706A unwinds the third articulation cable 406 to return the end effector 200 to a position substantially coaxial with the shaft assembly 600A (e.g., coaxial with the roll axis RA).

The fourth articulation puck assembly 708 includes a fourth articulation puck 708A, a fourth capstan 708B, and a fourth torsion spring 708C. The fourth articulation puck 708A is provided on an outer face of the lower frame 700B and directly engages the robotic platform 2000. The fourth capstan 708B is coupled to the fourth articulation puck 708A and winds the third articulation cable 408 therearound. The fourth capstan 708B is rotationally affixed to a fourth pivot pin 732 (which is integral with the fourth articulation puck 708A). The fourth capstan 708B is biased by a fourth torsion spring 708C in a retracting direction to maintain a minimum level of tension in the third articulation cable 408. As the fourth articulation puck assembly 708 does not include any gearing, the diameter of the fourth capstan 708B is what dictates the mechanical advantage achieved.

In use, and for example, rotation of the fourth capstan 708B by the robotic platform 2000, via the fourth articulation puck 708A, in a first direction winds the fourth articulation cable 408 around the fourth capstan 708B, which results in the end effector 200 pivoting downwards and to the right about the articulation joint 300. As discussed earlier, this downwards movement of the end effector 200 is compensated for in the knife firing subsystem by the differential 520. Rotation in the opposite direction by the fourth articulation puck 708A unwinds the fourth articulation cable 408 to return the end effector 200 to a position substantially coaxial with the shaft assembly 600A (e.g., coaxial with the roll axis RA).

Of course, and as discussed above, synchronous movement of various combinations of the puck assemblies 702, 704, 706, 708 enables the clinician (via the robotic platform 2000) to position the end effector 200 at any orientation.

Further to the above, the shaft roll puck assembly 710 includes a shaft roll puck 710A, a first screw gear 710B, and a second screw gear 710C. The shaft roll puck 710A is provided on an outer face of the lower frame 700B, is integral with a fifth pivot pin 734, and directly engages the robotic platform 2000. The first screw gear 710B is coaxial with and rotatable with the shaft roll puck 710A. The second screw gear 710C is meshed with the first screw gear 710B and coupled with the rotatable outer shaft 602.

In use, and for example, rotation of the first screw gear 710B by the robotic platform 2000, via the shaft roll puck 710A, in a first direction turns the second screw gear 710C to roll the outer shaft 602 (e.g., in a clockwise direction about the roll axis RA), as discussed in greater detail above. Rotation of the first screw gear in an opposite second direction causes the outer shaft 602 to roll in an opposite direction (e.g., a counterclockwise direction about the roll axis RA).

The disclosed technology described herein can be further understood according to the following clauses:

Clause 1: A differential assembly (520) for a knife firing subsystem (500) of a surgical instrument, the differential assembly (520) comprising: a carrier (526) extending along a longitudinal axis; a pinion gear (528) supported by the carrier (526) and configured to engage with a rack gear (522) in mechanical communication with a push rod (504); and a fin (540) extending transversely outward from the carrier (526) and configured to support the push rod (504).

Clause 2: The differential assembly (520) of clause 1, wherein the fin (540) is positioned a distance away from a proximal end of the push rod (504).

Clause 3: The differential assembly (520) of clause 1 or clause 2, wherein the fin (540) is configured to increase a buckling strength of the push rod (504) by at least 70 lbs.

Clause 4: The differential assembly (520) of any one of clauses 1-3, wherein the fin (540) is a first fin and the push rod (504) is a first push rod, the differential assembly (520) further comprising: a second fin (542) extending transversely outward from the carrier (526) in a direction opposite from the first fin (540), the second fin (542) configured to support a second push rod (506).

Clause 5: The differential assembly (520) of clause 4, wherein the rack gear (522) is a first rack gear and the pinion gear (528) is configured to engage with a second rack gear (524) in mechanical communication with the second push rod (506).

Clause 6: The differential assembly (520) of clause 4 or clause 5, wherein the second fin (542) is positioned a distance away from a proximal end of the second push rod (506).

Clause 7: The differential assembly (520) of any one of clauses 4-6, wherein the carrier (526) is in mechanical communication with a firing rod (502) of the knife firing subsystem (500) such that, when the firing rod (502) is moved proximally or distally, the pinion gear (528) moves the first push rod (504) and the second push rod (506) proximally or distally together.

Clause 8: A knife firing subsystem (500) for a surgical instrument comprising: a knife (206) configured to move proximally or distally in an end effector (200); a push rod (504) in mechanical communication with the knife (206); a rack gear (522) in mechanical communication with the push rod (504); a carrier (526) extending along a longitudinal axis; a pinion gear (528) supported by the carrier (526) and configured to engage with the rack gear (522) such that, when the carrier (526) is moved proximally or distally, the knife (206) is moved proximally or distally; and a fin (540) extending transversely outward from the carrier (526) and configured to support the push rod (504).

Clause 9: The knife firing subsystem (500) of clause 8, wherein the fin (540) is positioned a distance away from a proximal end of the push rod (504).

Clause 10: The knife firing subsystem (500) of clause 8 or clause 9, wherein the fin (540) is configured to increase a buckling strength of the push rod (504) by at least 70 lbs.

Clause 11: The knife firing subsystem (500) of any one of clauses 8-10, wherein the fin (540) is a first fin and the push rod (504) is a first push rod, the knife firing subsystem (500) further comprising: a second fin (542) extending transversely outward from the carrier (526) in a direction opposite from the first fin (540), the second fin (542) configured to support a second push rod (506).

Clause 12: The knife firing subsystem (500) of clause 11, wherein the rack gear (522) is a first rack gear and the pinion gear (528) is configured to engage with a second rack gear (524) in mechanical communication with the second push rod (506).

Clause 13: The knife firing subsystem (500) of clause 11 or clause 12, wherein the second fin (542) is positioned a distance away from a proximal end of the second push rod (506).

Clause 14: The knife firing subsystem (500) of any one of clauses 11-13, wherein the carrier (526) is in mechanical communication with a firing rod (502) of the knife firing subsystem (500) such that, when the firing rod (502) is moved proximally or distally, the pinion gear (528) moves the first push rod (504) and the second push rod (506) proximally or distally together.

Clause 15: The knife firing subsystem (500) of any one of clauses 8-14 further comprising a firing rod (502) configured to cause the carrier (526) to move proximally or distally.

Clause 16: The knife firing subsystem (500) of any one of clauses 11-15, wherein the pinion gear (528) permits relative axial movement between the first push rod (504) and the second push rod (506).

Clause 17: The knife firing subsystem (500) of any one of clauses 12-16, wherein the first rack gear (522) and the second rack gear (524) are movable in opposing axial directions relative to one another in response to rotation of the end effector (200) about a pitch axis (PA).

Clause 18: The knife firing subsystem (500) of any one of clauses 8-17, wherein the carrier (526) is rotatably coupled to the firing rod (502), thereby permitting the carrier (526) to rotate axially with respect to the firing rod (502).

Clause 19: The knife firing subsystem (500) of any one of clauses 11-18, wherein the first push rod (504) comprises a first flexible section (508) and the second push rod (504) comprises a second flexible section (510).

Clause 20: The knife firing subsystem (500) of clause 19, wherein the first flexible section (508) comprises a first push coil (508) and the second flexible section (510) comprises a second push coil (510).

Clause 21: The knife firing subsystem (500) of clause 20, further comprising: a first center cable (512) extending through the first push coil (508); and a second center cable (514) extending through the second push coil (510).

Clause 22: The knife firing subsystem (500) of any one of clauses 19-21, wherein the first push rod (504) further comprises a first rigid rod (516) axially aligned with and coupled to the first flexible section (508), and the second push rod (506) further comprises a second rigid rod (518) axially aligned with and coupled to the second flexible section (510).

Clause 23: The knife firing subsystem (500) of any one of clauses 8-22, wherein the firing rod (502) is in mechanical communication with a firing puck (712) configured to engage with a robotic platform (2000).

The embodiments described above are cited by way of example, and the present invention is not limited by what has been particularly shown and described hereinabove. Rather, the scope of the invention includes both combinations and sub combinations of the various features described and illustrated hereinabove, as well as variations and modifications thereof which would occur to persons skilled in the art upon reading the foregoing description and which are not disclosed in the prior art.

What is claimed is:

1. A differential assembly for a knife firing subsystem of a surgical instrument, the differential assembly comprising:

a carrier extending along a longitudinal axis;

a pinion gear supported by the carrier and configured to engage with a rack gear in mechanical communication with a push rod; and a fin extending transversely outward from the carrier and configured to support the push rod.

2. The differential assembly of claim 1, wherein the fin is positioned a distance away from a proximal end of the push rod.

3. The differential assembly of claim 1, wherein the fin is configured to increase a buckling strength of the push rod by at least 70 lbs.

4. The differential assembly of claim 1, wherein the fin is a first fin and the push rod is a first push rod, the differential assembly further comprising:

a second fin extending transversely outward from the carrier in a direction opposite from the first fin, the second fin configured to support a second push rod.

5. The differential assembly of claim 4, wherein the rack gear is a first rack gear and the pinion gear is configured to engage with a second rack gear in mechanical communication with the second push rod.

6. The differential assembly of claim 4, wherein the second fin is positioned a distance away from a proximal end of the second push rod.

7. The differential assembly of claim 4, wherein the carrier is in mechanical communication with a firing rod of the knife firing subsystem such that, when the firing rod is moved proximally or distally, the pinion gear moves the first push rod and the second push rod proximally or distally together.

8. A knife firing subsystem for a surgical instrument comprising:

a knife configured to move proximally or distally in an end effector;

a push rod in mechanical communication with the knife;

a rack gear in mechanical communication with the push rod;

a carrier extending along a longitudinal axis;

a pinion gear supported by the carrier and configured to engage with the rack gear such that, when the carrier is moved proximally or distally, the knife is moved proximally or distally; and a fin extending transversely outward from the carrier and configured to support the push rod.

9. The knife firing subsystem of claim 8, wherein the fin is positioned a distance away from a proximal end of the push rod.

10. The knife firing subsystem of claim 8, wherein the fin is configured to increase a buckling strength of the push rod by at least 70 lbs.

11. The knife firing subsystem of claim 8, wherein the fin is a first fin and the push rod is a first push rod, the knife firing subsystem further comprising:

a second fin extending transversely outward from the carrier in a direction opposite from the first fin, the second fin configured to support a second push rod.

12. The knife firing subsystem of claim 11, wherein the second fin is positioned a distance away from a proximal end of the second push rod.

13. The knife firing subsystem of claim 11, wherein the rack gear is a first rack gear and the pinion gear is configured to engage with a second rack gear in mechanical communication with the second push rod.

14. The knife firing subsystem of claim 11, wherein the carrier is in mechanical communication with a firing rod of the knife firing subsystem such that, when the firing rod is moved proximally or distally, the pinion gear moves the first push rod and the second push rod proximally or distally together.

15. The knife fire subsystem of claim 14, wherein the pinion gear permits relative axial movement between the first push rod and the second push rod.

16. The knife firing subsystem of claim 13, wherein the first rack gear and the second rack gear are movable in opposing axial directions relative to one another in response to rotation of the end effector about a pitch axis (PA).

17. The knife firing subsystem of claim 11, wherein the first push rod comprises a first flexible section and the second push rod comprises a second flexible section.

18. The knife firing subsystem of claim 17, wherein the first flexible section comprises a first push coil and the second flexible section comprises a second push coil.

19. The knife firing subsystem of claim 14, wherein the carrier is rotatably coupled to the firing rod, thereby permitting the carrier to rotate axially with respect to the firing rod.

20. The knife firing subsystem of claim 14, wherein the firing rod is configured to cause the carrier to move proximally or distally.

* * * * *